US012663415B2

(12) United States Patent

Diwu et al.

(10) Patent No.: US 12,663,415 B2
(45) Date of Patent: Jun. 23, 2026

(54) CHROMOGENIC AND FLUOROGENIC COMPOUNDS AND THEIR USE FOR BIOLOGICAL DETECTION

(71) Applicant: AAT Bioquest, Inc., Sunnyvale, CA (US)

(72) Inventors: Zhenjun Diwu, Sunnyvale, CA (US); Qinglin Meng, Sunnyvale, CA (US); Ruogu Peng, San Jose, CA (US); Qin Zhao, Sunnyvale, CA (US)

(73) Assignee: AAT Bioquest, Inc., Sunnyvale, CA (US)

(*) Notice: Subject to any disclaimer, the term of this patent is extended or adjusted under 35 U.S.C. 154(b) by 951 days.

(21) Appl. No.: 17/701,399

(22) Filed: Mar. 22, 2022

(65) Prior Publication Data

US 2024/0272146 A1 Aug. 15, 2024

(51) Int. Cl.
*G01N 33/52* (2006.01)
*C07H 17/04* (2006.01)
*G01N 33/68* (2006.01)

(52) U.S. Cl.
CPC ............ *G01N 33/52* (2013.01); *C07H 17/04* (2013.01); *G01N 33/6803* (2013.01)

(58) Field of Classification Search
USPC ........................................................ 536/18.1
See application file for complete search history.

(56) References Cited

U.S. PATENT DOCUMENTS 4,557,862 A * 12/1985 Mangel ................ C07K 5/0808 530/331
4,640,893 A 2/1987 Mangel et al.
11,104,926 B1 8/2021 Sulikowski et al.

FOREIGN PATENT DOCUMENTS

WO WO-2005007663 A2 * 1/2005 ............ C07H 21/04

OTHER PUBLICATIONS

Liu et al., "Fluorescent Molecular Probes V: A Sensitive Caspase-3 Substrate for Fluorometric Assays," *Bioorganic & Medicinal Chemistry Letters*, vol. 9, Issue 22, Nov. 15, 1999, pp. 3231-3236.

* cited by examiner

*Primary Examiner* — Traviss C Mcintosh, III
(74) *Attorney, Agent, or Firm* — Fenwick & West LLP

(57) ABSTRACT

The disclosure provides chromogenic and fluorogenic compounds comprising amino acid or peptide appendages that are capable of detecting an activity in a bioassay. Also provided herein are methods for detecting a biological activity in a sample with the subject chromogenic and fluorogenic compounds. In one embodiment, provided herein is a method for detecting endotoxin in a sample. Further provided herein are kits including the subject chromogenic and fluorogenic compounds for detecting a biological activity in a sample.

15 Claims, 5 Drawing Sheets

Specification includes a Sequence Listing.

SEQUENCE LISTING

<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Glu Val Asp
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Leu Val Tyr
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Leu Val Tyr
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Glu His Asp
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Leu Arg Gly Gly
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Lys Lys Ala Gly
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Lys Ala Gly Gly
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Asp Glu Val Asp
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Leu Leu Val Tyr
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Leu Glu His Asp
1

<210> SEQ ID NO 12

-continued

<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Leu Arg Gly Gly
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Lys Lys Ala Gly
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Lys Ala Gly Gly
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Arg Ala Glu Ile
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Asp Val Glu Asp
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Ile Asp Ala Arg
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Asp Thr Glu Ile
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Tyr Val Leu Leu
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Asp His Glu Leu
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Ile Asp Ala Arg
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Leu Glu His Asp
1

<210> SEQ ID NO 23
<211> LENGTH: 4
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 23

Asp Glu Val Asp
1


<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Glu Thr Asp
1


<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys His Leu Tyr
1
```

CHROMOGENIC AND FLUOROGENIC COMPOUNDS AND THEIR USE FOR BIOLOGICAL DETECTION

FIELD OF THE DISCLOSURE

The disclosure relates in general to chromogenic and fluorogenic protease substrates useful for analyte detection. This disclosure relates to a method of preparing and using protease substrates that generate color or become highly fluorescent upon enzymatic hydrolysis. This disclosure finds use in detection and identification of microorganisms, sterilization assurance, pharmaceutical discovery, enzyme assays, immunoassays, and other biological tests.

SEQUENCE LISTING

The instant application contains a Sequence Listing which has been submitted electronically in ASCII format and is hereby incorporated by reference in its entirety. Said ASCII copy, created on Sep. 22, 2023, is named 51842US_CRF_sequencelisting.txt and is 4,922 bytes in size.

INTRODUCTION

Proteases are a class of enzymes that catalytically hydrolyze peptide bonds. Their primary chemical sequence and unique three-dimensional structure determine their activity and specificity. Depending on the active site composition, proteases are classified into major groups including aspartic, metallo-, thiol-, and serine proteases. The role of proteases in physiological processes is widely recognized. Proteases constitute a large and important group of enzymes involved in such diverse physiological processes as blood coagulation, inflammation, reproduction, fibrinolysis, and the immune response. Not only are they involved in such functions as digestion, blood coagulation and fibrinolysis (see e.g., R. Lottenberg, et al., Methods in Enzymology 1981, 80, 341-361), but also in ovulation, tumorigenicity, immune response, and viral and bacterial infection, etc. (see e.g., D. C. Livingston, et al., Biochem. 1981, 20, 4298-4306). For example, retroviruses such as HIV are known to encode a protease which functions to process precursor proteins at specific cleavage sites. These cleavages occur during the virion assembly and are required for the maturation of infectious virus particles. Thus, inhibition of these proteases has become an important target for the design of antiviral agents, including those for AIDS and Covid-19. In addition, public awareness of antibiotic resistant bacteria strains and food-borne illnesses is greatly increasing in recent years. The management of microbial risks in healthcare, cosmetics, food and beverage industries is a serious health and safety issue. Bacterial testing is an integral part of managing microbial risks. The ability of many bacteria to produce proteases is a widely used criterion for identification and characterization of certain pathogenic species.

Numerous disease states are caused by and can be characterized by the alterations in the activity of specific proteases and their inhibitors. Measurement of these alterations are therefore clinically significant in the treatment and management of the underlying disease states. Proteases, however, are not easy to assay with their natural substrates, the assays are difficult to perform and monitor. With currently available synthetic substrates, the assays are expensive, insensitive, and in some cases nonselective. Furthermore, with the use of either the naturally occurring substrate or the presently available synthetic substrates, high concentrations of the target protease are required which results, in part, in the self-destruction of the protease. Finally, there are very few choices of colors for the simultaneously multiplexing test of multiple protease activities in a single assay due to the limited availability of chromogenic or fluorogenic substrates of different colors.

Sensitive and quantitative enzyme assays are required for the discovery and understanding of biological functions of proteases, the diagnosis of physiological disorders and the development of therapeutical drugs. A variety of techniques have been used to measure protease activities, including enzyme-linked immunosorbent assays (ELISA), high performance liquid chromatography (HPLC), protein immunoblot analysis, and thin layer electrophoretic analysis. However, these methods usually required multiple steps, require multiple reagents, and are slow and expensive to operate. They are sometimes impractical for applications such as high-throughput screening of pharmaceutical drugs, e.g., protease inhibitors.

Chromogenic substrates are molecules that change from weakly colored or colorless to highly colored upon enzymatic hydrolysis. The color can be readily observed by naked eyes or with a device such as a spectrophotometer, a diode, or a microplate plate reader. Fluorogenic substrates are the molecules that change from weakly fluorescent or nonfluorescent to highly fluorescent upon enzymatic hydrolysis. They are widely used as molecular probes for studies and tests of viral and bacterial proteases, nucleases, saccharides, phosphatases, kinases and other enzymes (see e.g., M. Manafi et al., Microbiological Reviews, 1991, 55, 335-348). The fluorescence can be readily observed under UV, visible or infrared illumination, by a fluorescent microscope, in a microwell plate reader, or in a flow cytometer.

U.S. Pat. Nos. 4,557,862 and 4,640,893 describe enzyme assay substrates derived from rhodamine 110. The enzyme substrates disclosed in U.S. Pat. Nos. 4,557,862 and 4,640,893 have their maximum fluorescence shorter than 530 nm where there is severe autofluorescence resulting from a variety of biological samples to be tested. The rhodamine 110 substrates tend to have high background noise for certain biological samples. In addition, there is no evident color changes resulting from the protease-induced hydrolysis of rhodamine 110 enzyme substrates.

U.S. Pat. No. 11,104,926 disclose some rhodamine derivatives that were used for detecting esterase activities. However, the compounds of U.S. Pat. No. 11,104,926 were not intended or active for detecting protease activities (See Liu et al, Bioorg. Med. Chem Lett., 1999, 3231-3236).

New chromogenic and fluorogenic protease substrates with higher extinction coefficients that can be detected at higher wavelengths and with low background noise are of interest.

SUMMARY

The disclosure provides chromogenic and fluorogenic compounds comprising amino acid or peptide appendages that are capable of detecting an analyte in a bioassay. Also provided herein are methods for detecting a biological activity in a sample with the subject chromogenic and fluorogenic compounds. In one embodiment, provided herein is a method for detecting endotoxin in a sample. Further provided herein are kits including the subject chromogenic and fluorogenic compounds for detecting a biological activity in a sample.

The new rhodamine derivatives of the present invention have several characteristics that render them useful as protease substrates. These substrates are colorless and nonfluorescent and have small extinction coefficients, thus having low assay background noise. The protease-induced hydrolysis of the substrates gives the rhodamine products that have both absorption and fluorescence dramatically shifted to much longer wavelength with a large increase in fluorescence intensity and a large extinction coefficient to that of previously known rhodamine derivatives. The dramatic color change of the substrates caused by a protease can be clearly seen by naked eyes, making them ideal compounds for use in rapid diagnostic applications that do not require a sophisticated instrument to read the optical signal change.

The subject chromogenic and fluorogenic compounds have a masked chromophore and/or fluorophore moiety core that can be characterized as a rhodamine lactone core flanked by two amino acid or peptide appendages. The amino acid or peptide appendages can be substrates for a target enzyme that provide for cleavage of the appendages from the core moiety, thus releasing the detectable chromophore and/or fluorophore, e.g., a rhodamine-based chromophore and/or fluorophore. The target enzyme can be an analyte that is targeted for detection and/or assessment in a sample. Alternatively, the enzyme can be an indirect reporter of the presence of a target analyte in a sample.

Accordingly, in a first aspect there is provided a chromogenic and/or fluorogenic compound having a structure of Formula 1:

Formula 1

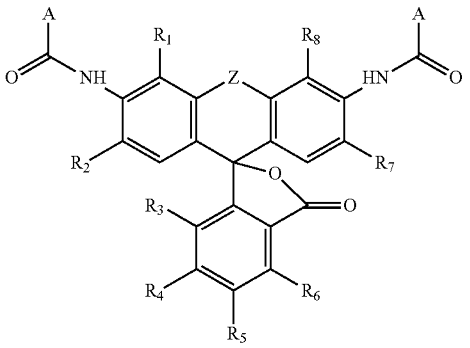

or a salt thereof, wherein:

- each A is an amino acid or a peptide fragment (e.g., a substrate for a target enzyme) connected to a masked chromophore and/or fluorophore moiety via an enzyme-cleavable amide bond;
- $R_1$ to $R_8$ are each independently selected from hydrogen, halogen, a carboxy, an alkyl, a substituted alkyl, an aryl, a substituted aryl, a heteroaryl group, and a substituted heteroaryl group; and
- Z is selected from O, $C(R_{10}R_{11})$, $Si(R_{10}R_{11})$, S=O, O=S=O, N—$R_{11}$, P—$R_{11}$, O=P—$R_{11}$, O=P—$OR_{11}$, OH—B—OH or $B(OR_{10}OR_{11})$, wherein $R_{10}$ and $R_{11}$ are independently selected from hydrogen, an alkyl, a substituted alkyl, an aryl, a substituted aryl, a heteroaryl group and a substituted heteroaryl group, with the proviso that when Z is O, each A is a peptide fragment comprising an arginine (Arg) residue connecting the peptide fragment to the amide group, and at least three other amino acids; and
- wherein the compound is capable of releasing a detectable chromophore and/or fluorophore in the presence of a target enzyme or analyte that provides for cleavage of the enzyme-cleavable amide bonds.

In some embodiments, the chromogenic and/or fluorogenic compound has a structure of formula 2:

(2)

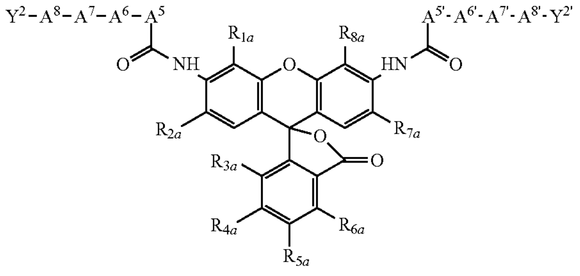

or a salt thereof, wherein:

- $A^5$ and $A^{5'}$ are each arginine (Arg);
- $A^6$-$A^8$ and $A^{6'}$-$A^{8'}$ are each independently selected from an amino acid;
- $Y^2$ and $Y^{2'}$ are each a terminal group; and
- $R^{1a}$-$R^{8a}$ are each independently selected from hydrogen, halogen, a carboxy, an alkyl, a substituted alkyl an aryl, a substituted aryl, a heteroaryl group and a substituted heteroaryl group.

BRIEF DESCRIPTION OF THE DRAWINGS

The foregoing and other features and advantages of the present embodiments will be more fully understood from the following detailed description of illustrative embodiments taken in conjunction with the accompanying drawings in which.

DEFINITIONS

Figure 1:
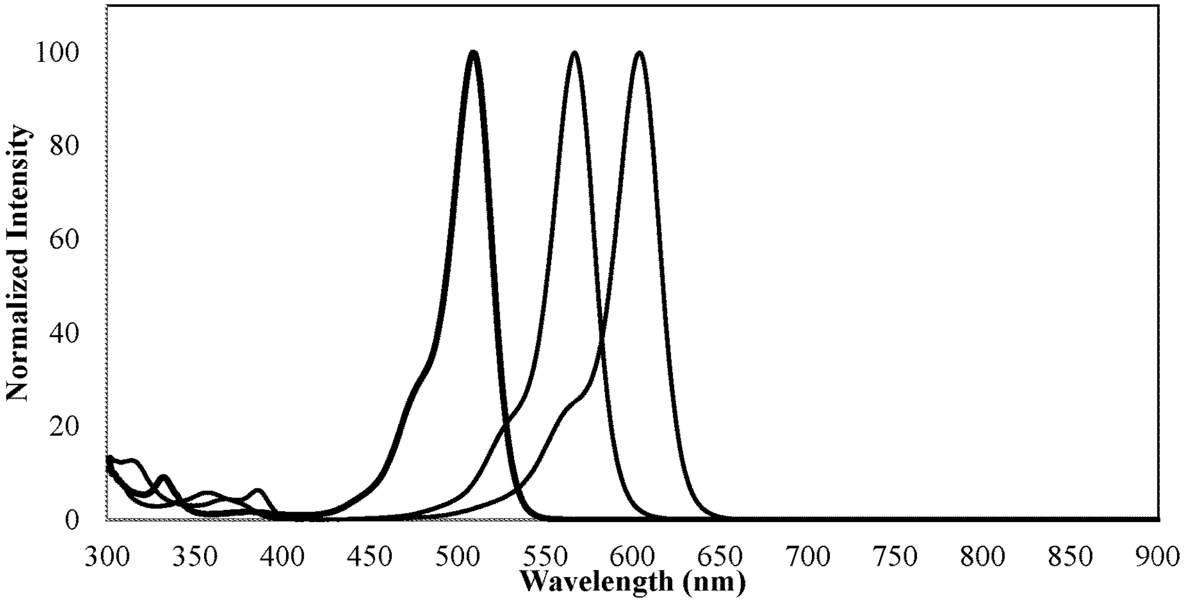
FIG. 1. Illustrates the normalized absorption spectrum of rhodamine 110, 2-(6-amino-3-iminio-10,10-dimethyl-3,10-dihydroanthracen-9-yl)benzoate (CR110) and 2-(7-amino-3-iminio-5,5-dimethyl-3,5-dihydrodibenzo[b,e]silin-10-yl) benzoate (SR110) in PBS buffer (pH=7.4).
Figure 2:
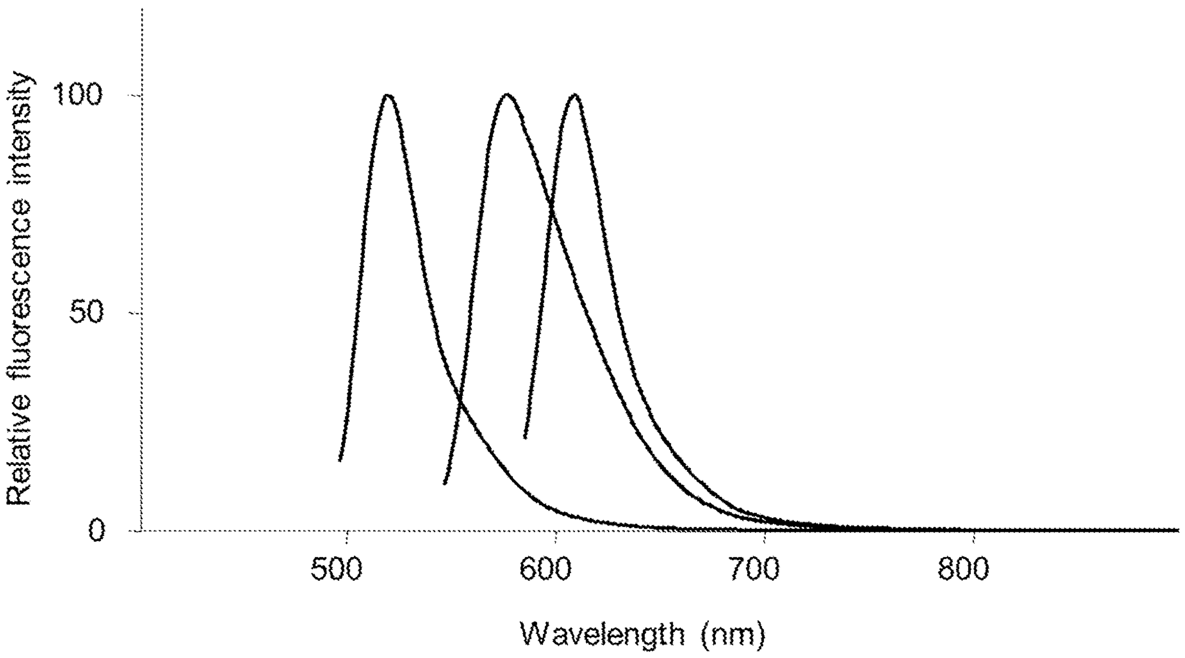
FIG. 2. Illustrates the normalized fluorescence spectrum of rhodamine 110, 2-(6-amino-3-iminio-10,10-dimethyl-3,10-dihydroanthracen-9-yl)benzoate (CR110) and 2-(7-amino-3-iminio-5,5-dimethyl-3,5-dihydrodibenzo[b,e]silin-10-yl)benzoate (SR110) in PBS buffer (pH=7.4).
Figure 3:
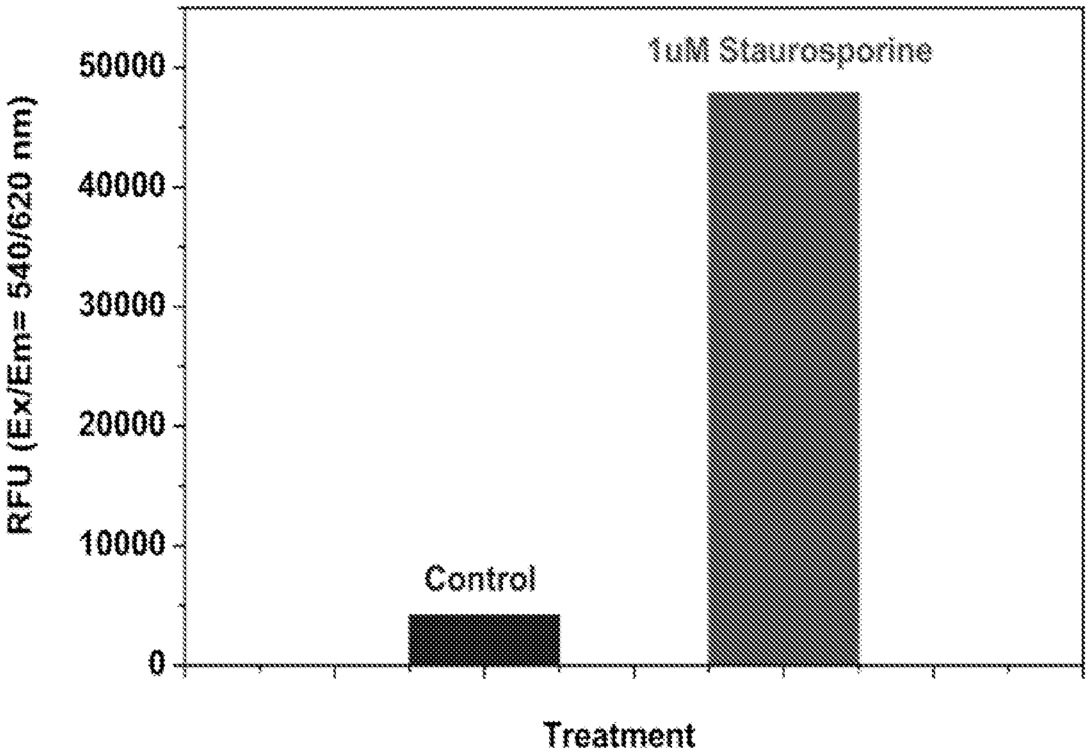
FIG. 3. Illustrates the detection of Caspase 3/7 activities in Jurkat cells with Compound 4. Jurkat cells are seeded on the same day at 200,000 cells/90 μL/well in a Costar black wall/clear bottom 96-well plate. The cells are treated with or without 1 μM of staurosporine for 5 hours. The caspase 3/7 working solution (100 μL/well) are added and incubated at room temperature for 1 hour. The fluorescence intensity is measured at Ex/Em=540/620 nm (Cutoff=610 nm) with FlexStation fluorescence microplate reader.

Before the present invention is described in further detail, it is to be understood that this invention is not limited to the particular molecules, methodologies, devices, solutions or apparatuses described, as such methods, devices, solutions or apparatuses can, of course, vary. It is also to be understood that the terminology used herein is for the purpose of describing particular embodiments only and is not intended to limit the scope of the present invention. The following definitions are set forth to illustrate and define the meaning and scope of the various terms used to describe the invention herein.

Use of the singular forms "a" "an" and "the" include plural references unless the context clearly dictates otherwise. Thus, for example, reference to "a probe" includes a plurality of probes, and the like. Additionally, use of specific plural references, such as "two" "three" etc., read on larger numbers of the same subject unless the context clearly dictates otherwise.

The term "chromogenic" as used herein, refers to color change from weakly colored or colorless to highly colored upon enzymatic hydrolysis. The color change can be readily observed by naked eyes or with a device such as a spectrophotometer, a diode, or a microplate plate reader.

The term "fluorogenic" as used herein, refers to fluorescence change from weakly fluorescent or nonfluorescent to highly fluorescent upon enzymatic hydrolysis. The fluorescence change can be readily observed under UV, visible or infrared illumination, by a fluorescent microscope, in a microwell plate reader, or in a flow cytometer.

The term "alkyl" as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others. In some embodiments, an alkyl group includes from 1 to 20 carbon atoms. In some embodiments, an alkyl group includes from 1 to 10 carbon atoms. In certain embodiments, an alkyl group includes from 1 to 6 carbon atoms, such as from 1 to 4 carbon atoms.

The term "substituted alkyl" refers to an alkyl group as defined herein wherein one or more carbon atoms in the alkyl chain have been optionally replaced with a heteroatom such as —O—, —N—, —S—, $—S(O)_n—$ (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, $—SO_2$-alkyl, $—SO_2$-aryl, $—SO_2$-heteroaryl, and $—NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "aryl" as employed herein, by itself or as part of another group, refers to an aryl or aromatic ring system containing 1 to 10 unsaturated rings (each ring containing 6 conjugated carbon atoms and no heteroatoms) that are optionally fused to each other or bonded to each other by carbon-carbon single bonds, which is optionally further substituted as described below. Examples of aryl ring systems include, but are not limited to, substituted or unsubstituted derivatives of fluorenyl, phenyl, biphenyl, o-, m-, or p-terphenyl, 1-naphthyl, 2-naphthyl, 1-, 2-, or 9-anthryl, 1-, 2-, 3-, 4-, or 9-phenanthrenyl, 1-perylenyl, 1-ovalenyl, 1-benzoperylene, 1- or 2-chrysenyl, 1- or 2-hexahelicenyl, 1-corannulenyl, 1-coronenyl, 1-, 2- or 4-pyrenyl. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

The term "heteroaryl" as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups.

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The term "carboxy" as used herein, by itself or as part of another group, is represented by —COOW wherein W is a hydrogen, an alkali metal ion, an ammonium or other biologically compatible counter ion.

The term "sulfonate" as used herein, by itself or as part of another group, is represented by $—S(=O)_2OW$ wherein W is a hydrogen, an alkali metal ion, an ammonium or other biologically compatible counter ion.

The term "phosphonate" as used herein, by itself or as part of another group, is represented by $—P(=O)O_2W_2$ wherein W is a hydrogen, an alkali metal ion, an ammonium or other biologically compatible counter ion.

The term "boronate" as used herein, by itself or as part of another group, is represented by —$B(OW)_2$ wherein W is a hydrogen, an alkali metal ion, an ammonium or other biologically compatible counter ion.

The term "ammonium" as used herein, by itself or as part of another group, is represented —$N(R_3)X$ wherein n is 1-20, R is a short alkyl (e.g., $C_1$-$C_{12}$ alkyl); X is a biologically compatible anion such as $F^-$, $Cl^-$, $Br^-$ or $I^-$. Ammonium may include a nitrogen ring structure such as pyridinium, acridinium or quinolinium etc.

The term "sulfonium" as used herein, by itself or as part of another group, is represented —$S(R_2)X$ wherein n is 1-20, R is a short alkyl (e.g., $C_1$-$C_{12}$ alkyl); X is a biologically compatible anion such as $F^-$, $Cl^-$, $Br^-$ or $I^-$.

The term "phosphonium" as used herein, by itself or as part of another group, is represented —$P(R_3)X$ wherein n is 1-20, R is a short alkyl (e.g., $C_1$-$C_{12}$ alkyl); X is a biologically compatible anion such as $F^-$, $Cl^-$, $Br^-$ or $I^-$.

The terms "protease" or "peptidase" or "proteinase" as employed herein, refers to an enzyme that catalyzes proteolysis, the breakdown of proteins into smaller polypeptides or single amino acids. They do this by cleaving the peptide bonds within proteins by hydrolysis, a reaction where water breaks bonds.

As used herein, "peptide" and "protein" encompass amino acid sequences of a length that include as few as 2 amino acid residues. "Peptides" and "proteins" include molecules made intracellularly and molecules made cell-free. "Peptides" and "proteins" also include molecules with natural or semi-synthetic or artificial sequences, which sequences may contain amino acids that are not present in natural proteins. For example, "peptide" and "protein" include (i) a native peptide, (ii) a biologically active fragment of the native peptide, (iii) a biologically active peptide analog of the native peptide, (iv) a biologically active variant of the native peptide, (v) a peptide with an artificial sequence containing a biologically active consensus sequence, or (vi) a peptide with a completely artificial sequence The amino acid sequence of a recombinant or non-recombinant peptide having an amino acid sequence such as As used herein, "amino acid" includes natural amino acids and amino acids that do not exist in natural proteins. In addition, amino acid derivatives are also included, which include acylated amino acids, proteases, hydrolyzed amides and esters. Thus, an important requirement for labeled protease substrates is the presence of bonds that are hydrolyzed by the protease. In general, the expressions "protein", "peptide" and "amino acid" should be construed to include all derivative molecules capable of providing one or more bonds that are hydrolyzed by proteases.

The term "sample" refers to a material or mixture of materials, in some cases in liquid form, containing one or more analytes of interest. The term can refer to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample".

The terms "determining," "measuring," and "assessing," and "assaying" are used interchangeably and include both quantitative and qualitative determinations.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by the following Detailed Description.

DETAILED DESCRIPTION

As summarized above, the present disclosure provides chromogenic and fluorogenic compounds comprising amino acid or peptide appendages that are capable of detecting an analyte in a bioassay. Also provided herein are methods for detecting a biological activity in a sample with the subject chromogenic and fluorogenic compounds. In one embodiment, provided herein is a method for detecting endotoxin in a sample. Further provided herein are kits including the subject chromogenic and fluorogenic compounds for detecting a biological activity in a sample.

The chromogenic and fluorogenic compounds of this disclosure are described in greater detail below. Methods for detecting a biological activity in a sample with the subject compounds are also described. Further described are kits including the subject compounds for detecting a biological activity in a sample.

Chromogenic and Fluorogenic Compounds

The present disclosure is directed to chromogenic and fluorogenic protease substrates. In some embodiments, the subject protease substrate is a chromogenic and/or fluorogenic compound of Formula 1:

Formula 1

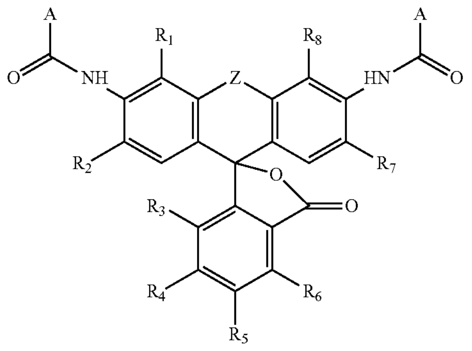

or a salt thereof, wherein:

each A is an amino acid or a peptide fragment connected to a masked chromophore and/or fluorophore moiety via an enzyme-cleavable amide bond;

$R_1$ to $R_8$ are each independently selected from hydrogen, halogen, a carboxy, an alkyl, a substituted alkyl, an aryl, a substituted aryl, a heteroaryl group, and a substituted heteroaryl group; and Z is selected from O, $C(R_{10}R_{11})$, $Si(R_{10}R_{11})$, S═O, O═S═O, N—$R_{11}$, P—$R_{11}$, O═P—$R_{11}$, O═P—$OR_{11}$, OH—B—OH or $B(OR_{10}OR_{11})$, wherein $R_{10}$ and $R_{11}$ are independently selected from hydrogen, an alkyl, a substituted alkyl, an aryl, a substituted aryl, a heteroaryl group and a substituted heteroaryl group, with the proviso that when Z is O, each A is a peptide fragment comprising an arginine (Arg) residue connecting the peptide fragment to the amide group, and at least three other amino acids; and wherein the compound is capable of releasing a detectable chromophore and/or fluorophore in the presence of a target enzyme or analyte that provides for cleavage of the enzyme-cleavable amide bonds.

In some embodiments of Formula 1, $R_1$ to $R_8$ are independently selected from H, F, Cl, a methyl, a carboxy. In some embodiments, $R_1$ to $R_8$ are each H.

In some embodiments of Formula 1, Z is independently selected from $C(R_{10}R_{11})$, and $Si(R_{10}R_{11})$. In some embodiments, $R_{10}$ and $R_{11}$ are an alkyl. In some cases, $R_{10}$ and $R_{11}$ are different. In some cases, $R_{10}$ and $R_{11}$ are the same. In some embodiments, the alkyl is a $C_1$-$C_3$ alkyl. In some cases, the alkyl is methyl.

In some embodiments of Formula 1, $R_1$ to $R_8$ are each H; Z is independently selected from $C(R_{10}R_{11})$, and $Si(R_{10}R_{11})$; and $R_{10}$ and $R_{11}$ are each methyl.

In some embodiments of Formula 1, A is a peptide fragment comprising one or more of an amino acid selected from Arg, Ala, Pro, D-Ala, Beta-Ala, and Asp.

In some embodiments of Formula 1, A is selected from Ac-Ala-Asn-Trp, Cbz-Asp-Glu-Val-Asp (SEQ ID NO: 1), Ac-Asp-Glu-Val-Asp (SEQ ID NO: 2), succinimidyl-Leu-Leu-Val-Tyr (SEQ ID NO: 3), Ac-Trp-Leu-Ala, Ac-Lys-Gln-Leu, Cbz-Leu-Leu-Glu, Ac-Pro-Ala-Leu, Ac-Ile-Thr-Asp, Ac-Arg-Arg-Arg, Boc-Leu-Leu-Val-Tyr (SEQ ID NO: 4), Ac-Leu-Glu-His-Asp (SEQ ID NO: 5), Gly-Pro, Cbz-Leu-Arg-Gly-Gly (SEQ ID NO: 6), Cbz-Lys-Lys-Ala-Gly (SEQ ID NO: 7), and Cbz-Lys-Ala-Gly-Gly (SEQ ID NO: 8).

In Some Embodiments of Formula 1, the Compound is of the Formula (1A):

In some embodiments of Formula 1A, $A^1$-$A^4$ and $A^{1'}$-$A^{4'}$ are each independently selected from an amino acid selected from Alanine (Ala), isoleucine (Ile), valine (Val), aspartic acid (Asp), glutamic acid (Glu) and arginine (Arg).

In some embodiments of Formula 1A, $A^1$-$A^4$ and $A^{1'}$-$A^{4'}$ are the same. In other embodiments, $A^1$-$A^4$ and $A^{1'}$-$A^{4'}$ are different.

In some embodiments of Formula 1A, n-o and n'-o' are each 1, such that the compound of Formula 1A is flanked by two peptides of 4 amino acids in length. In some embodiments, n, n', m and m' are each 1, and o and o' are each 0, such that the compound of Formula 1A is flanked by two peptides of 3 amino acids in length. In some cases, n and n' is 1, and m, m' o and o' are each 0, such that the compound of Formula 1 is flanked by a peptide of 2 amino acids in length. In some embodiments, n-o and n'-o' are each 0, such that the compound of Formula 1A is flanked by single amino acids.

In some embodiments of Formula 1A, $A^1$-$A^4$ and $A^{1'}$-$A^{4'}$ each represent a peptide fragment comprising one or more of an amino acid selected from Arg, Ala, Pro, D-Ala, Beta-Ala, and Asp.

In some embodiments of Formula 1A, n-o and n'-o' are each independently 0 or 1, and $A^1$-$A^4$ and $A^{1'}$-$A^{4'}$ are each independently a peptide fragment selected from Ala-Asn-Trp, Asp-Glu-Val-Asp (SEQ ID NO: 9), Leu-Leu-Val-Tyr (SEQ ID NO: 10), Trp-Leu-Ala, Lys-Gln-Leu, Leu-Leu-Glu, Pro-Ala-Leu, Ile-Thr-Asp, Arg-Arg-Arg, Leu-Glu-His-Asp (SEQ ID NO: 11), Gly-Pro, Leu-Arg-Gly-Gly (SEQ ID NO: 12), Lys-Lys-Ala-Gly (SEQ ID NO: 13), and Lys-Ala-Gly-Gly (SEQ ID NO: 14).

In certain embodiments of Formula 1A, n-o and n'-o' are each 1 and $A^1$-$A^4$ and $A^{1'}$-$A^{4'}$ are each selected from Asp-Glu-Val-Asp (SEQ ID NO: 9) and Arg-Ala-Glu-Ile (SEQ ID NO: 15).

(1A)

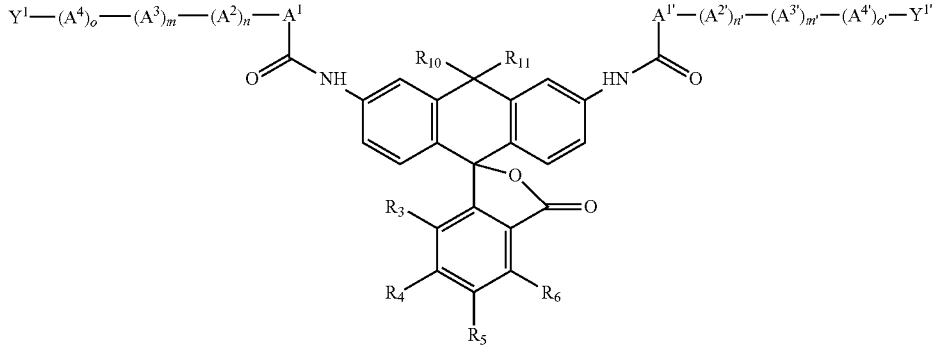

wherein:

$A^1$-$A^4$ and $A^{1'}$-$A^{4'}$ are each independently selected from an amino acid;

$Y^1$ and $Y^{1'}$ are each an optional terminal group;

$R_{10}$-$R_{11}$ are selected from H, alkyl and substituted alkyl; and n-o and n'-o' are each independently selected from 0 or 1.

In some embodiments of Formula 1A, $A^1$-$A^4$ and $A^{1'}$-$A^{4'}$ are each independently selected from an amino acid selected from Alanine (Ala), isoleucine (Ile), leucine (Leu), valine (Val), tryptophan (Trp), asparagine (Asn), glutamine (Gln), proline (Pro), glycine (Gly), lysine (Lys), aspartic acid (Asp), glutamic acid (Glu) and arginine (Arg), wherein the amino acid is of L-configuration or D-configuration.

In some embodiments of Formula 1A, $Y^1$ and $Y^{1'}$ are each independently selected from alkyl, alkoxy, aryl, heteroaryl, amino, acyl, ester, wherein any of the $Y^1$ or $Y^{1'}$ groups are optionally further substituted. In some embodiments, $Y^1$ and $Y^{1'}$ are independently selected from methyl, acetyl (Ac), benzyloxycarbonyl (Cbz), succinimidyl (Succ), and tert-butyloxycarbonyl (Boc). In some other embodiments, $Y^1$ and $Y^{1'}$ may be absent from Formula 1A. In some embodiments, $Y^1$ and $Y^{1'}$ are the same. In some embodiments, $Y^1$ and $Y^{1'}$ are different.

In some embodiments of Formula 1A, $R_{10}$-$R_{11}$ are each alkyl. In some cases, $R_{10}$ and $R_{11}$ are different. In some cases, $R_{10}$ and $R_{11}$ are the same. In some embodiments, the alkyl is a $C_1$-$C_3$ alkyl. In some cases, the alkyl is methyl.

In some embodiments of Formula 1A, $R_3$-$R_6$ are each H.

In some embodiments, the compound of Formula 1A is selected from one of the following structures:
(4) (SEQ ID NO: 16)
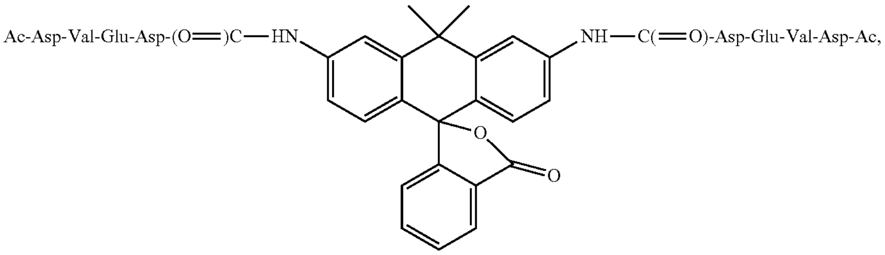
(5)
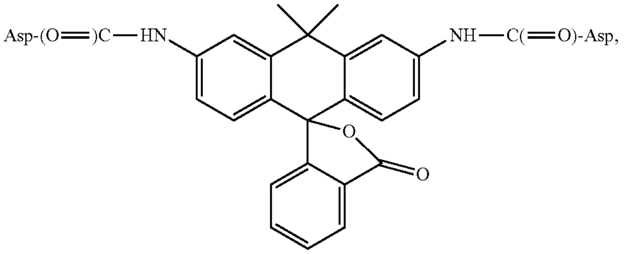
(6) (SEQ ID NO: 17)
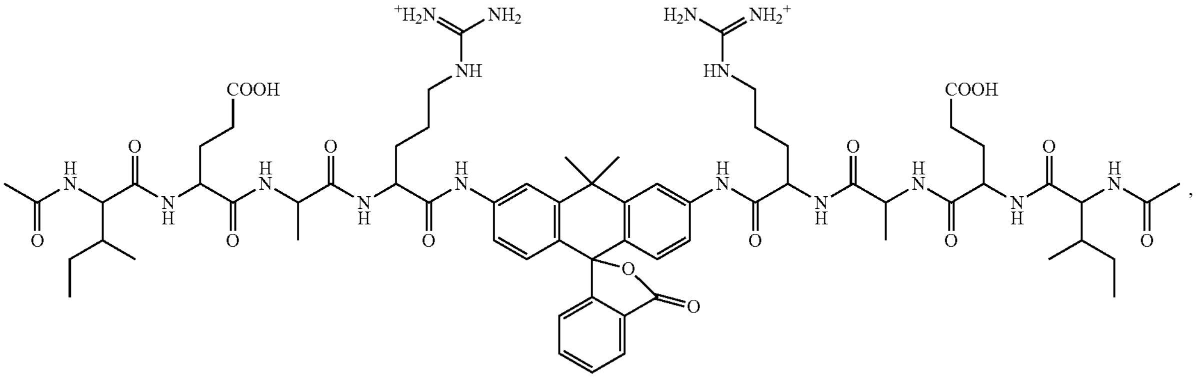
(20)
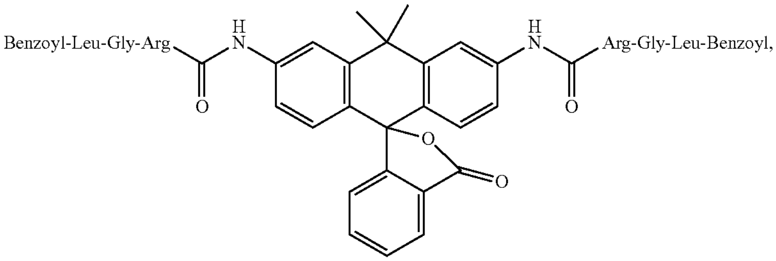
(21)
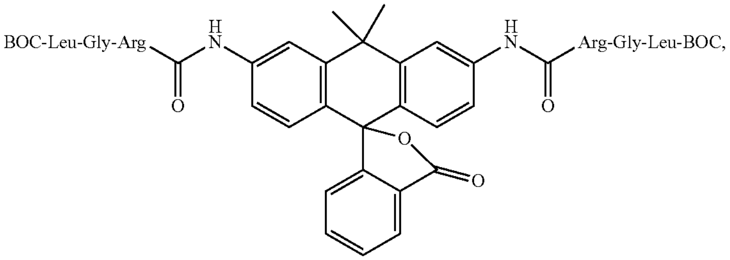

-continued
(26) (SEQ ID NO: 18)
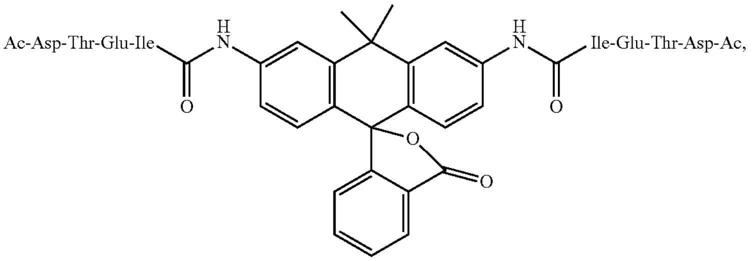
(30) (SEQ ID NO: 19)
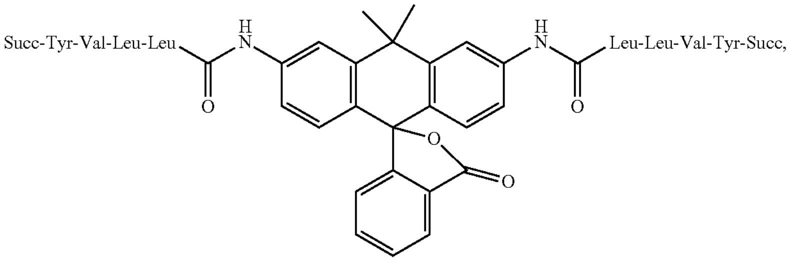
(31)
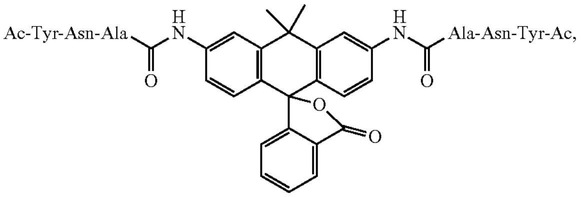
(34)
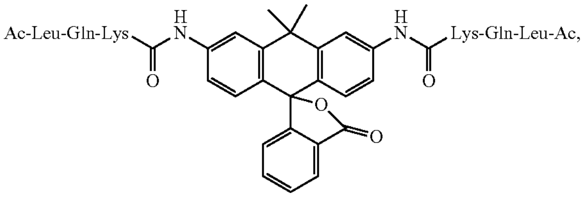
(35)
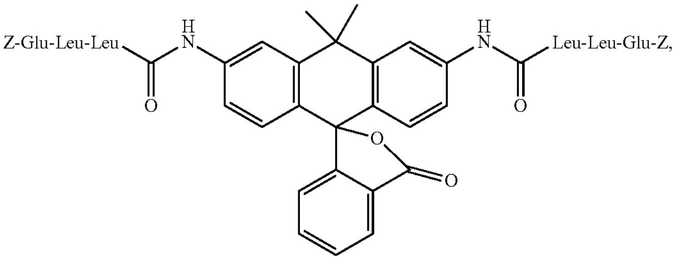
(36)
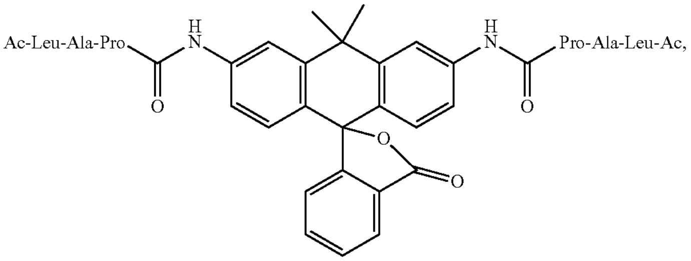
and
(37)
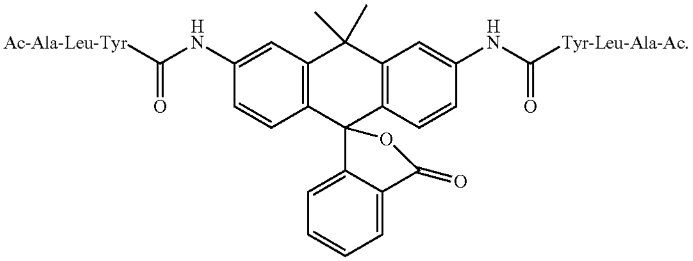

-continued

In some embodiments of Formula 1, the compound is of Formula 1B:

(IB)

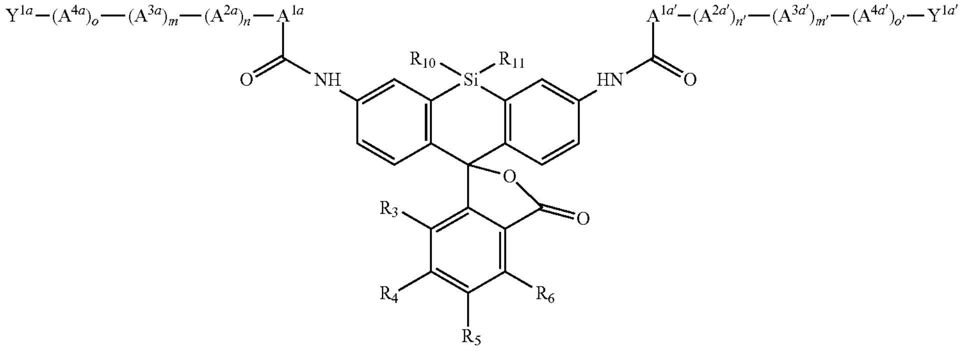

wherein:

$A^{1a}$-$A^{4a}$ and $A^{1a'}$-$A^{4a'}$ are each independently selected from an amino acid;

$Y^{1a}$ and $Y^{1a'}$ are each an optional terminal group;

$R_{10}$-$R_{11}$ are selected from H, alkyl and substituted alkyl; and n-o and n'-o' are each independently selected from 0 or 1.

In some embodiments of Formula 1B, $A^{1a}$-$A^{4a}$ and $A^{1a'}$-$A^{4a'}$ are each independently selected from an amino acid selected from Alanine (Ala), isoleucine (Ile), leucine (Leu), valine (Val), tryptophan (Trp), asparagine (Asn), glutamine (Gln), proline (Pro), glycine (Gly), lysine (Lys), aspartic acid (Asp), glutamic acid (Glu) histidine (His), and arginine (Arg).

In some embodiments of formula 1B, $A^{1a}$-$A^{4a}$ and $A^{1a'}$-$A^{4a'}$ are each independently selected from an amino acid selected from glycine (Gly), arginine (Arg), proline (Pro), valine (Val), lysine (Lys), leucine (Leu), histidine (His), and aspartic acid (Asp).

In some embodiments of formula 1B, $A^{1a}$-$A^{4a}$ and $A^{1a'}$-$A^{4a'}$ are the same. In other embodiments, $A^{1a}$-$A^{4a}$ and $A^{1a'}$-$A^{4a'}$ are different.

In some embodiments, n-o and n'-o' are each 1, such that the compound of Formula 1B is flanked by two peptides of 4 amino acids in length. In some embodiments, n, n', m and m' are each 1, and o and o' are each 0, such that the compound of Formula 1B is flanked by two peptides of 3 amino acids in length. In some cases, n and n' is 1, and m, m' o and o' are each 0, such that the compound of Formula 1B is flanked by two peptides of 2 amino acids in length. In some embodiments, n-o and n'-o' are each 0, such that the compound of Formula 1B is flanked by two single amino acid residues.

In some embodiments of Formula 1B, $A^{1a}$-$A^{4a}$ and $A^{1a'}$-$A^{4a'}$ each represent a peptide fragment comprising one or more of an amino acid selected from Arg, Ala, Pro, D-Ala, Beta-Ala, and Asp.

In some embodiments of Formula 1B, n-o and n'-o' are each independently 0 or 1, and $A^{1a}$-$A^{4a}$ and $A^{1a'}$-$A^{4a'}$ are each independently a peptide fragment selected from Ala-Asn-Trp, Asp-Glu-Val-Asp (SEQ ID NO: 9), Leu-Leu-Val-Tyr (SEQ ID NO: 10), Trp-Leu-Ala, Lys-Gln-Leu, Leu-Leu-Glu, Pro-Ala-Leu, Ile-Thr-Asp, Arg-Arg-Arg, Leu-Glu-His-Asp (SEQ ID NO: 11), Gly-Pro, Leu-Arg-Gly-Gly (SEQ ID NO: 12), Lys-Lys-Ala-Gly (SEQ ID NO: 13), and Lys-Ala-Gly-Gly (SEQ ID NO: 14).

In certain embodiments of Formula 1B, $A^{1a}$ and $A^{1a'}$ are each selected from glycine (Gly), arginine (Arg), leucine, and (Leu, proline (Pro).

In some embodiments of Formula 1B, $Y^{1a}$ and $Y^{1a'}$ are each independently selected from alkyl, alkoxy, aryl, heteroaryl, amino, acyl, ester, wherein any of the $Y^{1a}$ or $Y^{1a'}$ groups are optionally further substituted. In some embodiments, $Y^{1a}$ and $Y^{1a'}$ are independently selected from methyl, acetyl (Ac), benzyloxycarbonyl (Cbz), succinimidyl (Succ), and tert-butyloxycarbonyl (Boc). In some other embodiments, $Y^{1a}$ and $Y^{1a'}$ may be absent from Formula 1B. In some embodiments, $Y^{1a}$ and $Y^{1a'}$ are the same. In some embodiments, $Y^{1a}$ and $Y^{1a'}$ are different.

In some embodiments of Formula 1B, $R_{10}$-$R_{11}$ are each alkyl. In some cases, $R_{10}$ and $R_{11}$ are different. In some cases, $R_{10}$ and $R_{11}$ are the same. In some embodiments, the alkyl is a $C_1$-$C_3$ alkyl. In some cases, the alkyl is methyl.

In some embodiments of Formula 1B, $R_3$-$R_6$ are each H.

In some embodiments of Formula 1B, the compound is selected from one of the following structures:

(8)

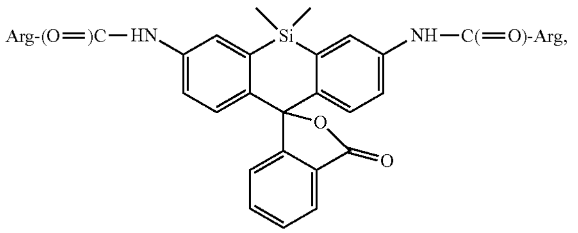

(9)

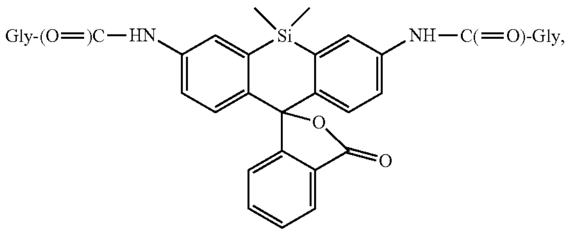

-continued (22)

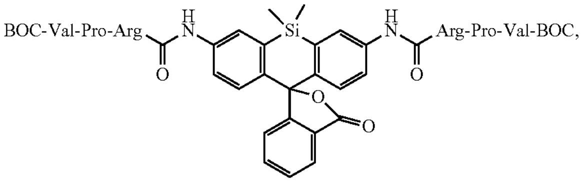

(23)

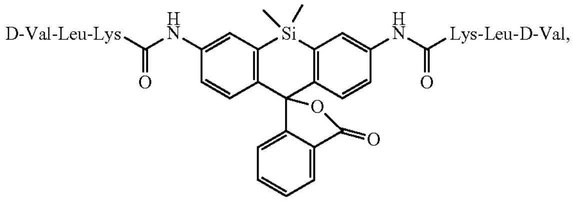

(27) (SEQ ID NO: 20)

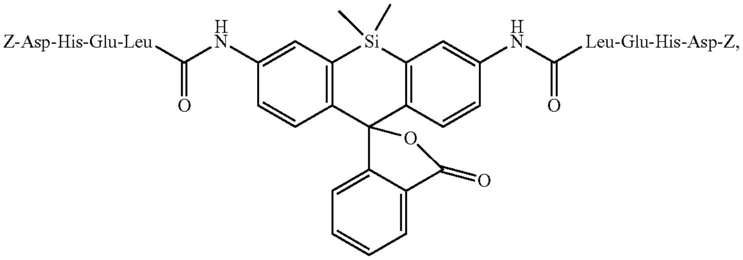

(28)

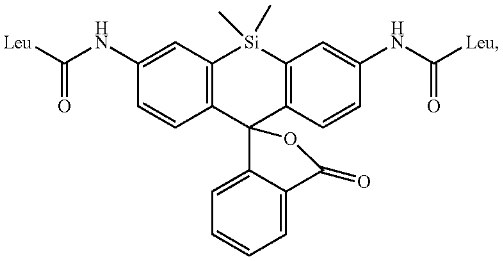

(32)

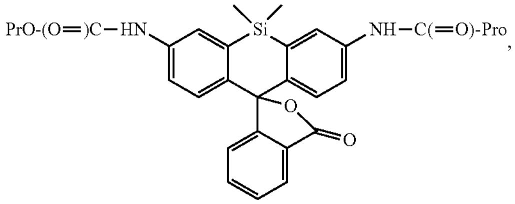

and (39)

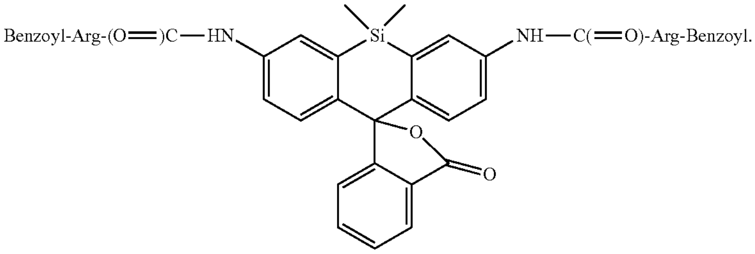

In some embodiments of any one of Formula 1-1B, the compound is capable of detecting a protease activity, an apoptosis or a cell viability in an appropriate bioassay. In some embodiments, the activity detected in the bioassay is selected from a biological activity listed in Table 1 (e.g., as disclosed herein below).

Also Provided Herein is a Compound of Formula 2:

(2)

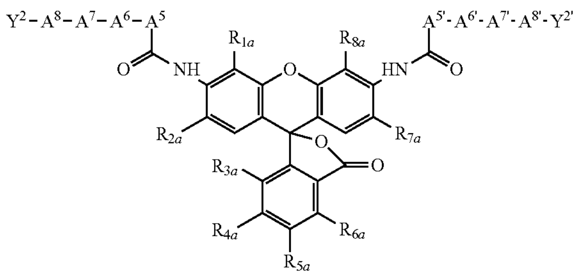

or a salt thereof, wherein:

$A^5$ and $A^{5'}$ are each arginine (Arg);

$A^6$-$A^8$ and $A^{6'}$-$A^{8'}$ are each independently selected from an amino acid;

$Y^2$ and $Y^{2'}$ is an optional terminal group; and $R^{1a}$-$R^{8a}$ are selected from hydrogen, halogen, a carboxy, an alkyl, a substituted alkyl an aryl, a substituted aryl, a heteroaryl group and a substituted heteroaryl group;

wherein the compound is capable of detecting an activity in a bioassay.

In some embodiments of the compound of Formula 2, $A^6$-$A^8$ and $A^{6'}$-$A^{8'}$ are each independently selected from arginine (Arg), alanine (Ala), glutamic acid (Glu), and isoleucine (Ile).

In some embodiments, $A^6$-$A^8$ and $A^{6'}$-$A^{8'}$ are the same. In some embodiments, $A^6$-$A^8$ and $A^{6'}$-$A^{8'}$ are each Ala-Glu-Ile.

In some embodiments of Formula 2, $R^{1a}$-$R^{8a}$ are each H.

In some embodiments of Formula 2, $Y^2$ and $Y^{2'}$ are each independently selected from alkyl, alkoxy, aryl, heteroaryl, amino, acyl, ester, wherein any of the $Y^2$-$Y^{2'}$ groups are optionally further substituted. In some embodiments, $Y^2$ and $Y^{2'}$ are independently selected from methyl, acetyl (Ac), benzyloxycarbonyl (Cbz), succinimidyl (Succ), and tert-butyloxycarbonyl (Boc). In some other embodiments, $Y^2$ and $Y^{2'}$ may be absent from Formula 2. In some embodiments, $Y^2$ and $Y^2$ are the same. In some embodiments, $Y^2$ and $Y^2$ are different.

In Some Embodiments of Formula 2, the Compound is of the Formula 2A:

biomolecules. Where the compound of the disclosure is positively charged, the counterion can be selected from, but is not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the disclosure is negatively charged, the counterion can be Formula 2A

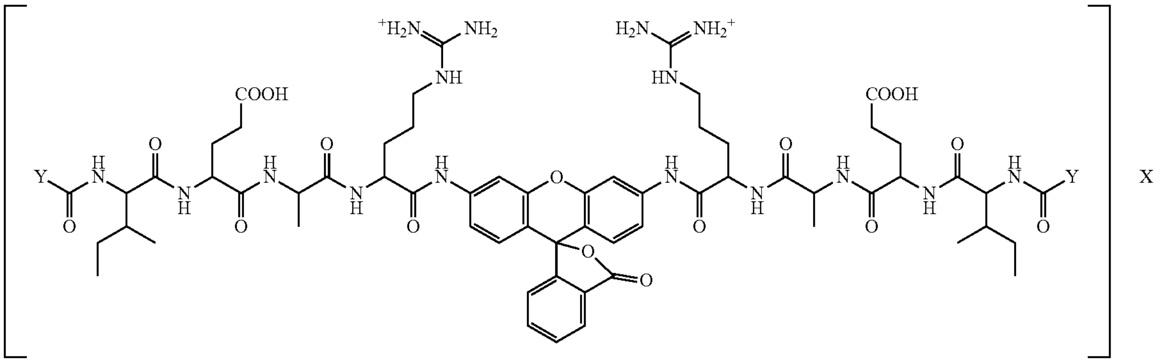

Wherein

X is a physiologically acceptable counter ion;

each Y is an alkyl, an aryl, a heteroaryl, an O-alkyl, an O-aryl, an O-heteroaryl, a NH-alkyl, a NH-aryl, or a NH-heteroaryl, wherein any of the Y groups are optionally substituted.

In some embodiments of Formula 2A, Y is a methyl, ethyl, $PhCH_2O$, or $(CH_3)_3CO$; and X is chloride, nitrate, iodide, fluoride, phosphate, sulfate, acetate, trifluoroacetate, borate or tetrafluoroborate.

In some embodiments of Formula 2A, the compound is of the following structure:

selected from, but is not limited to, alkali metal ions, alkaline earth metal ions, transition metal ions, ammonium or substituted ammonium or pyridinium ions. The subject counterion is biologically compatible, is not toxic, and does not have a substantially deleterious effect on biomolecules. Counterions may be readily changed by methods well known in the art, such as ion-exchange chromatography, or selective precipitation.

It is to be understood that the compounds or substrates of the disclosure have been drawn in one or another particular electronic resonance structure. Every aspect of the instant disclosure applies equally to compounds that are formally (SEQ ID NO: 17)

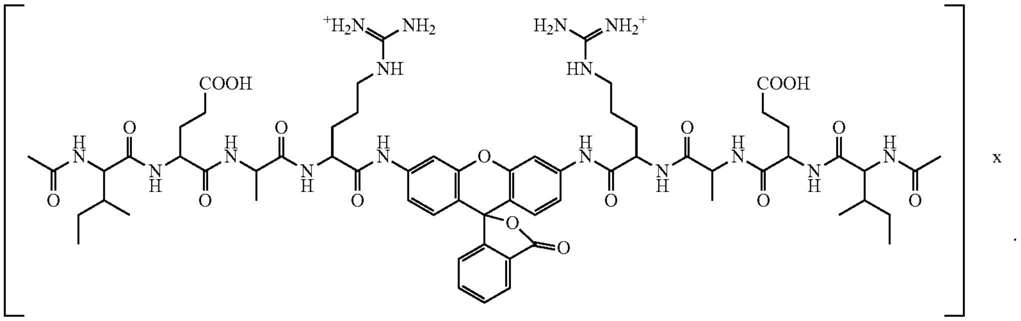

In some embodiments of Formula 2 or 2A, the compounds may exist in an inner salt.

In some embodiments of Formula 2 or 2A, the compound is capable of detecting an endotoxin activity in a bioassay.

Many embodiments of the compounds of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on drawn with other permitted resonance structures, as the electronic charge on the subject compounds is delocalized throughout the system itself.

At any time after or during staining, the sample is illuminated with a wavelength of light selected to give a detectable optical response and observed with a means for detecting the optical response. Equipment that is useful for illuminating the substrates of the disclosure includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The present disclosure provides new fluorogenic compounds that can be used for detecting protease activities. Proteases, or proteolytic enzymes, are involved in various biological events, such as biological events such as protein activation and cell signaling. Protease activity plays an important role in processes such as blood clotting, apoptosis and hormone regulation. Proteases are also essential for the activity of various viral and microbial pathogens. There is increasing interest in developing protease inhibitors for use as therapeutic agents in recent years.

Measurement of protease activity in biological samples can be used to analyze processes such as apoptosis, to screen for potential protease inhibitors, and to monitor sample purity, for example, during protein purification, is important. Proteases hydrolyze amides to produce peptides, single amino acids, labeled amino acid fragments, depending on the structure of the substrate and the identity of the enzyme. Protease activity can be measured using the synthetic peptide substrate analog labeled with a fluorophore or a chromophore disclosed herein. In some cases, the measurement of protease activity can also be performed using a single labeled amino acid. In these cases, protease activity is assayed by the ability of the protease to cleave the bond between a single amino acid and the fluorophore or chromophore present in the subject compounds. The subject chromogenic and fluorogenic compounds can be used to monitor or detect the activities of various proteases, including serine proteases, cysteine proteases, threonine proteases, aspartic proteases, glutamic proteases, metalloproteases, and asparagine peptide lyases etc.

Methods

Aspects of this disclosure include methods for detecting a biological activity in a sample. The present disclosure provides a method for assaying protease activity in a sample, the method comprising contacting a sample solution with a subject chromogenic or fluorogenic compound. The method includes a step of preparing conditions under which a protease present in a solution can decompose a subject compound (also referred to as a "protease substrate"), and a step of detection by color or fluorescence change. Information related to the marker is used as a convenience method to derive information regarding the presence or absence of protease activity or other biological activity.

Accordingly, in some embodiments there is provided a method of detecting a biological activity in a sample, the method comprising:

a) contacting the sample with a detection reagent comprising a subject chromogenic and/or fluorogenic compound (e.g., as described herein) under conditions in which said detection reagent releases the detectable chromophore and/or fluorophore in the presence of a target analyte, if present in the sample, to produce an optical signal; and b) assessing whether the target analyte is present in the sample by detecting the optical signal. In some embodiments of the method of detecting a biological activity in a sample, the target analyte is a protease. In certain cases, the method further comprises assessing a biological activity in the sample. In some embodiments, the biological activity is an apoptosis. In some embodiments, the biological activity is a cell viability.

In some embodiments, there is provided a method of determining an endotoxin level in a sample, comprising a) contacting said sample with a detection reagent comprising a subject chromogenic and/or fluorogenic compound (e.g., as described herein) under conditions in which said compound releases the detectable chromophore and/or fluorophore in the presence of endotoxin in the sample to produce an optical signal; and b) detecting the endotoxin level in the sample by detecting the optical signal.

In some embodiments of the method of determining an endotoxin level in a sample, the detection reagent comprises limulus amebocyte lysate (LAL) that is activated in the presence of endotoxin; and the compound is of claim 12.

The protease assays may be performed at room temperature. Depending on the water solubilities of the chromogenic or fluorogenic substrates, they might be first dissolved in a buffer or an organic solvent such as dimethylsulfoxide (DMSO) or ethanol to make a stock solution. Enzyme stock solutions can be serially diluted into an assay buffer immediately prior to being assayed. For most assays, an enzyme concentration might be chosen so that less than 10% of the substrate is hydrolyzed. The disclosed protease substrates exhibited a broad range of specificities as listed in Table 1. As shown in Table 1, the specificity exhibited by many proteinases depends to a large extend upon the interaction of subsite amino acids in the proteinase's active site with extended amino acid residues in the protease substrate. This can be characterized, with synthetic substrates, by observing variations in the specificity constant upon substituting or altering a single residue in the protease substrate. The present disclosure includes the synthesis of a series of chromogenic and fluorogenic compounds to assess their uses for detecting protease activities in terms of sensitivity, specificity and selectivity. The chromogenic and fluorogenic substrates of the present disclosure are extremely sensitive when tested upon the reactivity of the reactive-site bond and on the detectability of the leaving group as a hydrolysis product. Table 1 below depicts exemplary compounds of the disclosure, alongside the biological activity they are capable of detecting.

TABLE 1
The chromogenic and fluorogenic substrates, subject protease substrates and their associated biological activity
| Code | Structure | Biological Activity |
| --- | --- | --- |
| R110 | 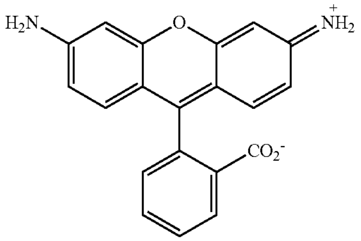 | Fluorophore |
| CR110 | 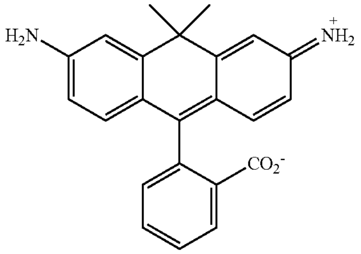 | Fluorophore |
| SiR110 | 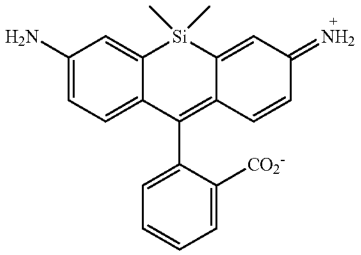 | Fluorophore |
| BR110 | 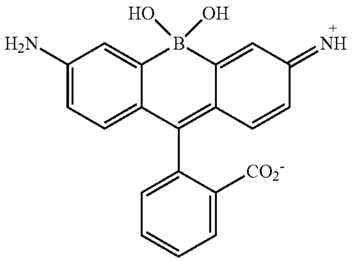 | Fluorophore |
| 4 (SEQ ID NO: 16) | 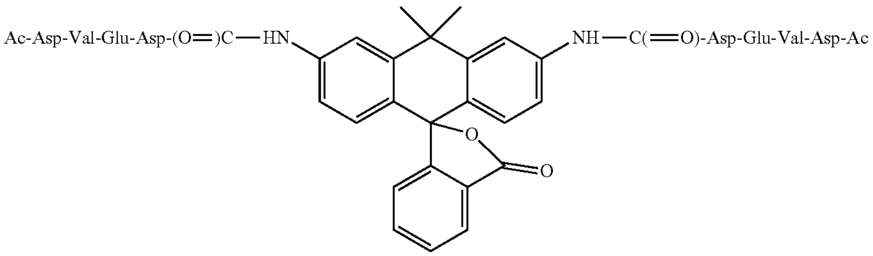 | Caspase 3/7 |

TABLE 1-continued
The chromogenic and fluorogenic substrates, subject protease substrates and their associated biological activity
| Code | Structure | Biological Activity |
|---|---|---|
| 5 | 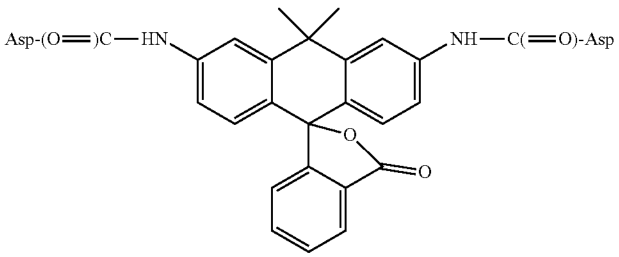 | Caspases |
| 6 (SEQ ID NO: 17) | 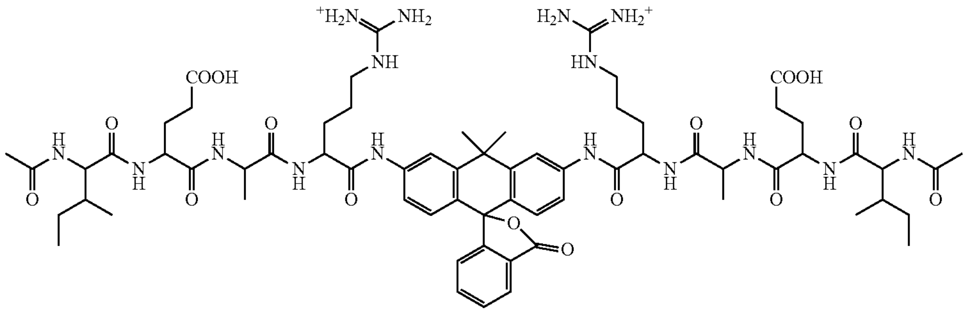 [SMILES: CCC(C)C(NC(C)=O)C(=O)NC(CCC(=O)O)C(=O)NC(C)C(=O)NC(CCCNC(N)=[NH2+])C(=O)Nc1ccc2c(c1)C(C)(C)c1cc(NC(=O)C(CCCNC(N)=[NH2+])NC(=O)C(C)NC(=O)C(CCC(=O)O)NC(=O)C(NC(C)=O)C(C)CC)ccc1C21OC(=O)c2ccccc21] | Endotoxin |
| 7 (SEQ ID NO: 21) | 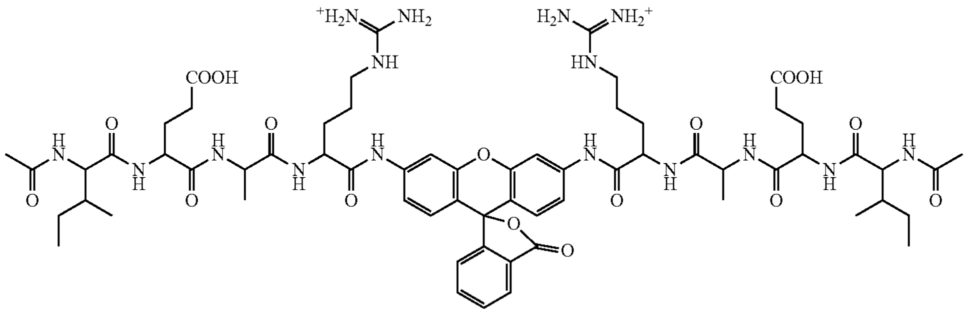 [SMILES: CCC(C)C(NC(C)=O)C(=O)NC(CCC(=O)O)C(=O)NC(C)C(=O)NC(CCCNC(N)=[NH2+])C(=O)Nc1ccc2c(c1)Oc1cc(NC(=O)C(CCCNC(N)=[NH2+])NC(=O)C(C)NC(=O)C(CCC(=O)O)NC(=O)C(NC(C)=O)C(C)CC)ccc1C21OC(=O)c2ccccc21] | Endotoxin |
| 8 | 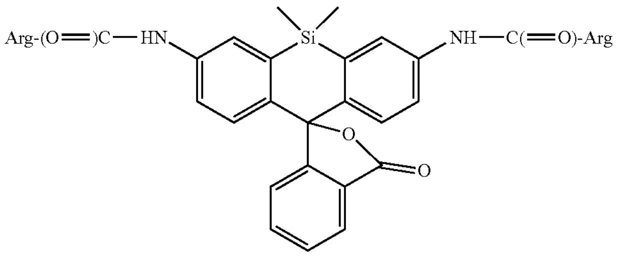 | Amino-peptidase, endopeptidase |
| 9 | 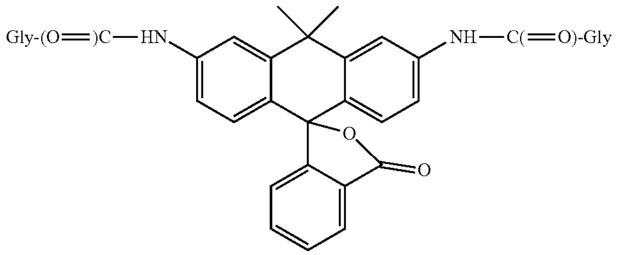 | Elastase |

TABLE 1-continued
The chromogenic and fluorogenic substrates, subject protease substrates and their associated biological activity
| Code | Structure | Biological Activity |
|---|---|---|
| 20 | 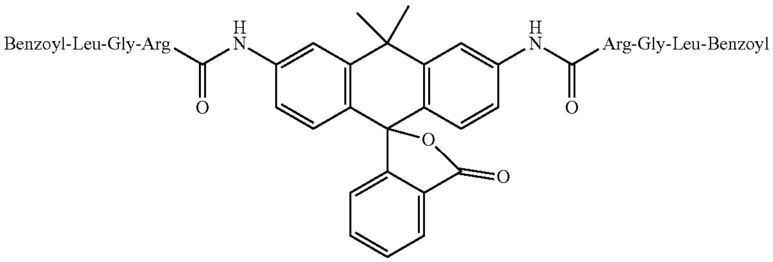 | C3/C5 convertases |
| 21 | 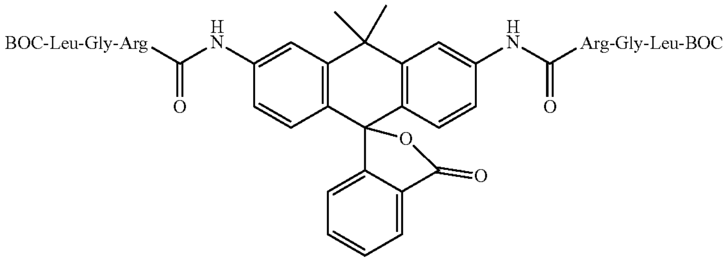 | C3/C5 convertases |
| 22 | 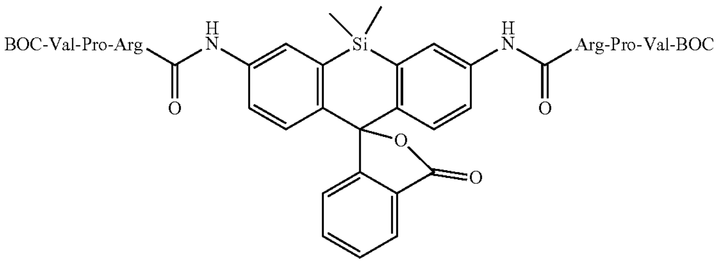 | Alpha-thrombin, methicillin-resistant Staphylo-coccus aureus (MRSA) |
| 23 | 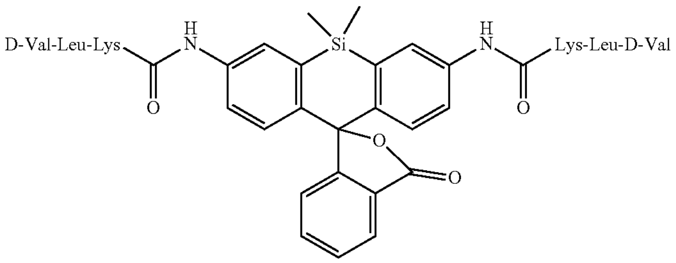 | plasmin |
| 24 | 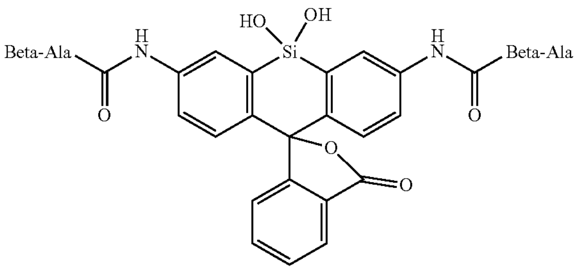 | Pancreatic elastase, arylamidase, beta-alanine amino-peptidase |

TABLE 1-continued
The chromogenic and fluorogenic substrates, subject protease substrates and their associated biological activity
| Code | Structure | Biological Activity |
|---|---|---|
| 25 | 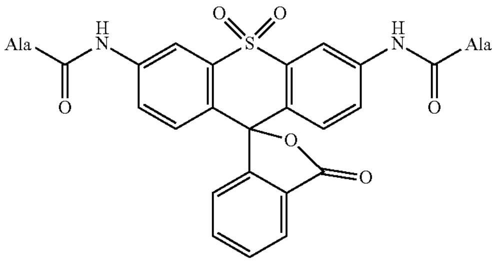 | Amino-peptidase, alanyl amino-peptidase, trypsin |
| 26 (SEQ ID NO: 18) | 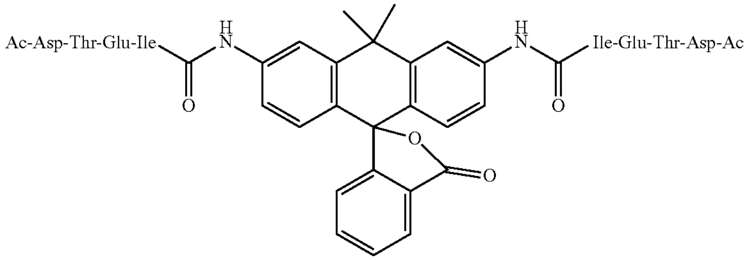 | Caspase-8, granzyme B |
| 27 (SEQ ID NO: 20) | 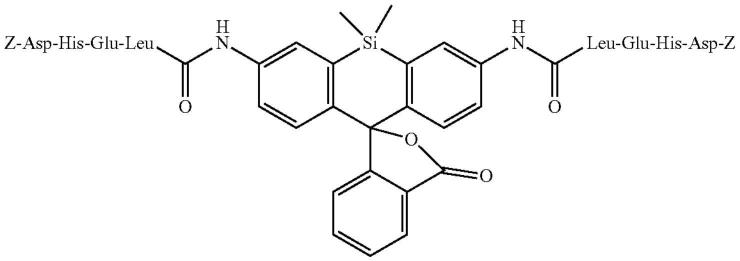 | Caspase 9 |
| 28 | 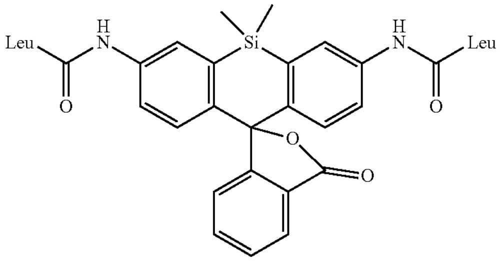 | Leucine amino-peptidase |
| 29 | 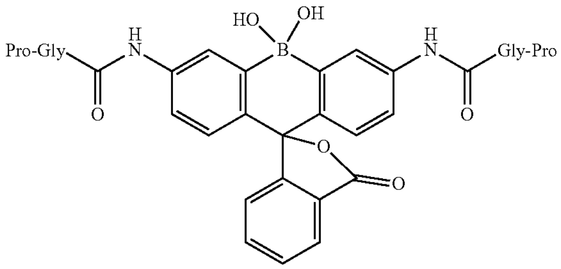 | Dipeptidyl peptidase IV (DPPIV) |

TABLE 1-continued
The chromogenic and fluorogenic substrates, subject protease substrates and their associated biological activity
| Code | Structure | Biological Activity |
|---|---|---|
| 30 (SEQ ID NO: 19) | 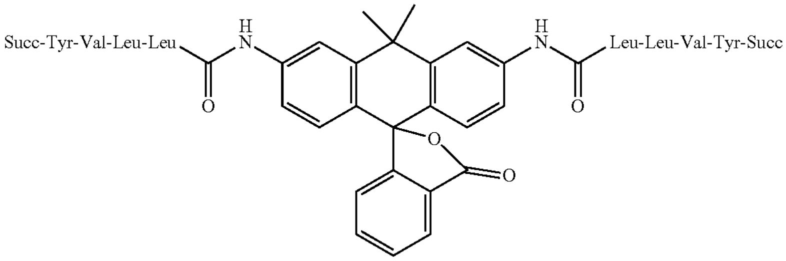 | 20S proteasome, calpains and other chymotrypsin-like proteases |
| 31 | 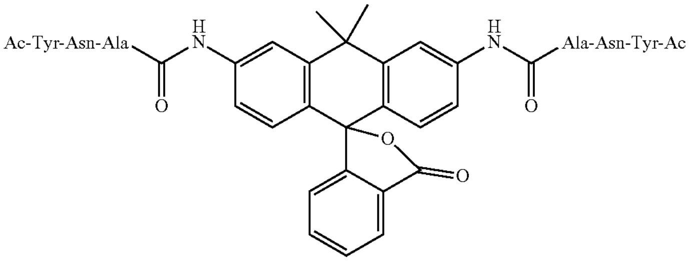 | Proteasome 20S-beta 5i |
| 32 | 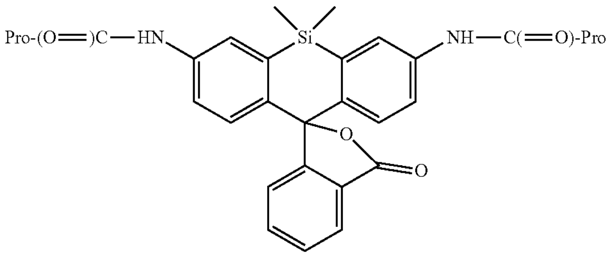 | Tricorn protease (TRI) |
| 33 | 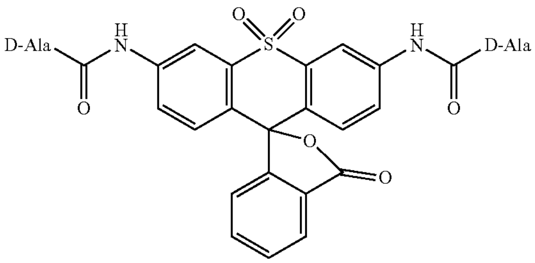 | amino-peptidase and endo-peptidase |
| 34 | 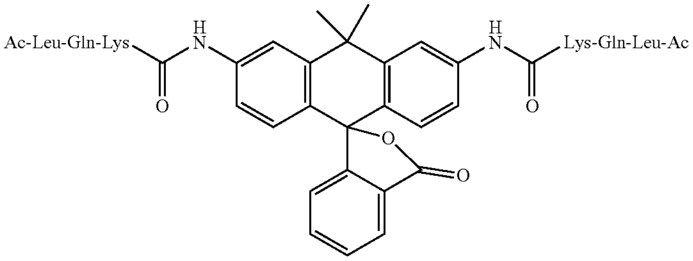 | Proteasome |

TABLE 1-continued

The chromogenic and fluorogenic substrates, subject protease substrates and their associated biological activity

| Code | Structure | Biological Activity |
|---|---|---|
| 35 | 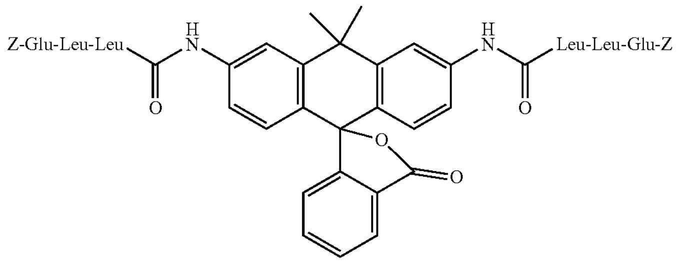 | Proteasome |
| 36 | 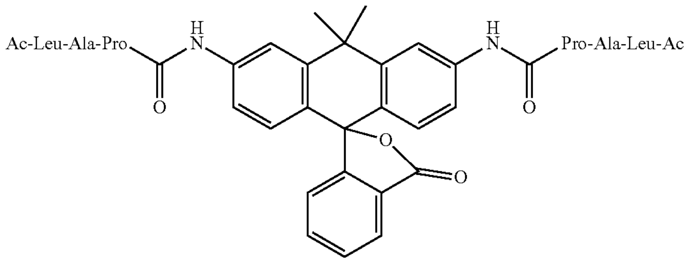 | Proteasome |
| 37 | 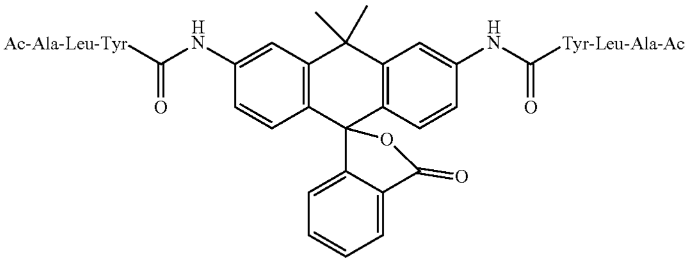 | Proteasome |
| 38 | 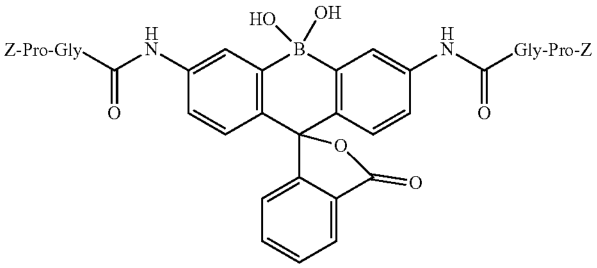 | Proline cleaving enzyme (prolyl endo-peptidase) |
| 39 | 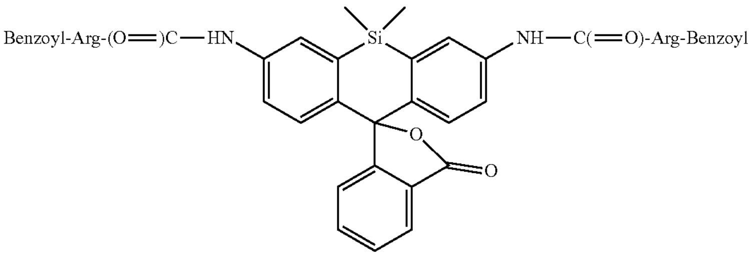 | Alpha-thrombin |

The activity of proteases is monitored by the optical changes resulting from the chromogenic or fluorogenic substrates or compounds of the present disclosure. The optical response is optionally detected by visual inspection, or by use of any of the following devices: CCD cameras, video cameras, photographic films, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

Kits

An aspect of the instant disclosure is the formulation of kits that facilitate the practice of various assays using any of the chromogenic or fluorogenic compounds of the disclosure, as described above. The kits of the disclosure can comprise a chromogenic or fluorogenic compound of the disclosure, where the compound is a specific indicator for a protease or a biological activity. The kit optionally further comprises one or more buffering agents, which can be present as an aqueous solution. The kits of the invention optionally further comprise one or more additional components selected from, additional detection reagents, luminescence standards, enzymes, enzyme inhibitors, organic solvent, and instructions for carrying out an assay of the invention.

Accordingly, in one embodiment there is provided a kit for detecting a biological activity in a sample, the kit comprising:

a) one or more subject chromogenic and/or fluorogenic compound (e.g., a chromogenic or fluorogenic protease substrate according to any one of formulae 1-2A); and b) one or more components selected from a buffer, an organic solvent, one or more detection reagents, luminescence standards, an enzyme, an enzyme indicator and an instruction sheet concerning the use of the kit for detecting a biological activity in a sample.

In Some Embodiments, the Subject Kit Comprises a) a compound of Formula 2A (e.g., compound 7 as described herein); and b) limulus amebocyte lysate (LAL) and an instruction sheet concerning the use of the kit for detecting endotoxin in a sample.

EMBODIMENTS

In addition to the appended claims, the clauses provided below illustrate several embodiments of this disclosure. They are not intended to limit or define the entire scope of the invention.

Clause 1. A chromogenic and/or fluorogenic compound having the structure of Formula Formula 1

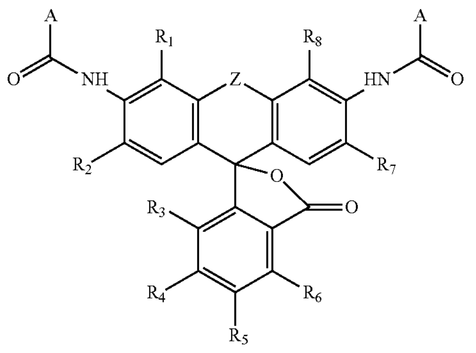

or a salt thereof, wherein:

each A is an amino acid or a peptide fragment connected to a masked chromophore and/or fluorophore moiety via an enzyme-cleavable amide bond;

$R_1$ to $R_8$ are each independently selected from hydrogen, halogen, a carboxy, an alkyl, a substituted alkyl, an aryl, a substituted aryl, a heteroaryl group, and a substituted heteroaryl group; and Z is selected from O, $C(R_{10}R_{11})$, $Si(R_{10}R_{11})$, S═O, O═S═O, N—$R_{11}$, P—$R_{11}$, O═P—$R_{11}$, O═P—$OR_{11}$, OH—B—OH or $B(OR_{10}OR_{11})$, wherein $R_{10}$ and $R_{11}$ are independently selected from hydrogen, an alkyl, a substituted alkyl, an aryl, a substituted aryl, a heteroaryl group and a substituted heteroaryl group, with the proviso that when Z is O, each A is a peptide fragment comprising an arginine (Arg) residue connecting the peptide fragment to the amide group, and at least three other amino acids; and wherein the compound is capable of releasing a detectable chromophore and/or fluorophore in the presence of a target enzyme or analyte that provides for cleavage of the enzyme-cleavable amide bonds.

Clause 2. The compound of clause 1, wherein:

$R_1$ to $R_8$ are independently selected from H, F, Cl, a methyl, and a carboxy;

Z is independently selected from $C(R_{10}R_{11})$, and $Si(R_{10}R_{11})$; and $R_{10}$ and $R_{11}$ are each alkyl.

Clause 3. The compound of clause 1, wherein:

each A is a peptide fragment comprising one or more amino acids selected from Arg, Ala, Pro, D-Ala, Beta-Ala and Asp;

$R_1$ to $R_8$ are each H; and

Z is independently selected from $C(R_{10}R_{11})$, and $Si(R_{10}R_{11})$, wherein $R_{10}$ and $R_{11}$ are each methyl.

Clause 4. The compound of clause 1, wherein:

each A is selected from Ac-Ala-Asn-Trp, Cbz-Asp-Glu-Val-Asp (SEQ ID NO: 1), Ac-Asp-Glu-Val-Asp (SEQ ID NO: 2), succinimidyl-Leu-Leu-Val-Tyr (SEQ ID NO: 3), Ac-Trp-Leu-Ala, Ac-Lys-Gln-Leu, Cbz-Leu-Leu-Glu, Ac-Pro-Ala-Leu, Ac-Ile-Thr-Asp, Ac-Arg-Arg-Arg, Boc-Leu-Leu-Val-Tyr (SEQ ID NO: 4), Ac-Leu-Glu-His-Asp (SEQ ID NO: 5), Gly-Pro, Cbz-Leu-Arg-Gly-Gly (SEQ ID NO: 6), Cbz-Lys-Lys-Ala-Gly (SEQ ID NO: 7), and Cbz-Lys-Ala-Gly-Gly (SEQ ID NO: 8);

$R_1$ to $R_8$ are each H; and

Z is independently selected from $C(R_{10}R_{11})$, and $Si(R_{10}R_{11})$, wherein $R_{10}$ and $R_{11}$ are each methyl.

Clause 5. The compound of clause 1, wherein the compound is of the formula (IA):

(IA)

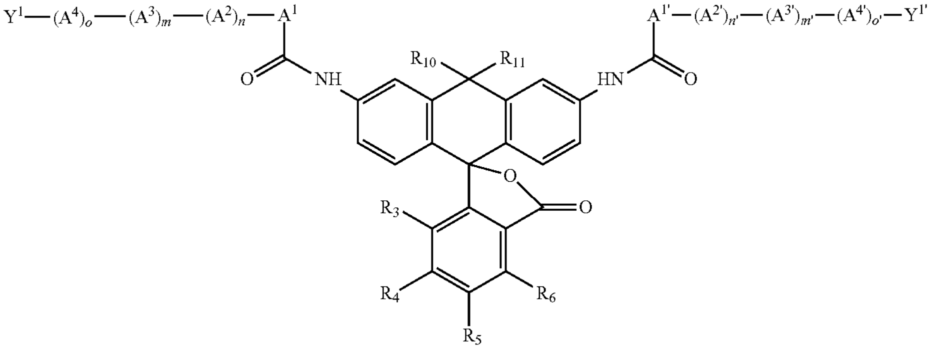

wherein:

$A^1$-$A^4$ and $A^{1'}$-$A^{4'}$ are each independently selected from an amino acid;

$Y^1$ and $Y^{1'}$ are each an optional terminal group;

$R_{10}$-$R_{11}$ are selected from H, alkyl and substituted alkyl; and n-o and n'-o' are each independently selected from 0 or 1.

Clause 6. The compound of clause 5, wherein $A^1$-$A^4$ and $A^{1'}$-$A^{4'}$ are each independently an amino acid selected from Alanine (Ala), isoleucine (Ile), leucine (Leu), valine (Val), tryptophan (Trp), asparagine (Asn), glutamine (Gln), proline (Pro), glycine (Gly), lysine (Lys), aspartic acid (Asp), glutamic acid (Glu) and arginine (Arg), wherein the amino acid is of L-configuration or D-configuration.

Clause 7. The compound of clause 6, wherein $A^1$-$A^4$ and $A^{1'}$-$A^{4'}$ are each independently an amino acid selected from Alanine (Ala), isoleucine (Ile), valine (Val), aspartic acid (Asp), glutamic acid (Glu) and arginine (Arg).

Clause 8. The compound of any one of clauses 5 to 7, wherein $A^1$-$A^4$ and $A^{1'}$-$A^{4'}$ are the same.

Clause 9. The compound of any one of clauses 5 to 8, wherein n-o and n'-o' are each 1.

Clause 10. The compound of clause 9, wherein $A^1$-$A^4$ and $A^{1'}$-$A^{4'}$ are each selected from Asp-Glu-Val-Asp (SEQ ID NO: 9) and Arg-Ala-Glu-Ile (SEQ ID NO: 15).

Clause 11. The compound of any one of clauses 5 to 10, wherein $Y^1$ and $Y^{1'}$ are each independently selected from alkyl, alkoxy, aryl, heteroaryl, amino, acyl, ester, wherein any of the $Y^1$ and $Y^{1'}$ groups are optionally further substituted.

Clause 12. The compound of any one of clauses 5 to 11, wherein $R^{10}$-$R^{11}$ are each alkyl.

Clause 13. The compound of clause 12, wherein each alkyl group is methyl.

Clause 14. The compound of any one of clauses 5 to 13, wherein $R_3$-$R_6$ are each H.

Clause 15. The compound of any one of clauses 5 to 14, selected from one of the following structures:

(4) (SEQ ID NO: 16)

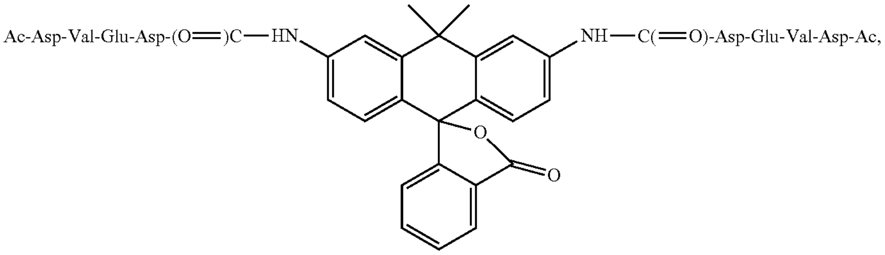

(5)

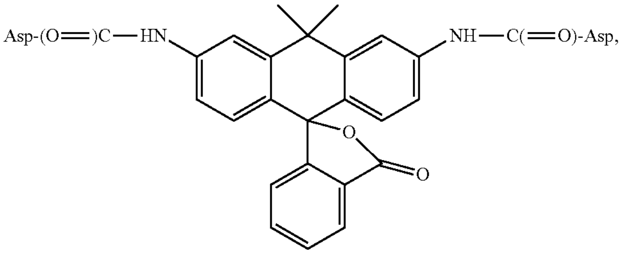

-continued
(6) (SEQ ID NO: 17)
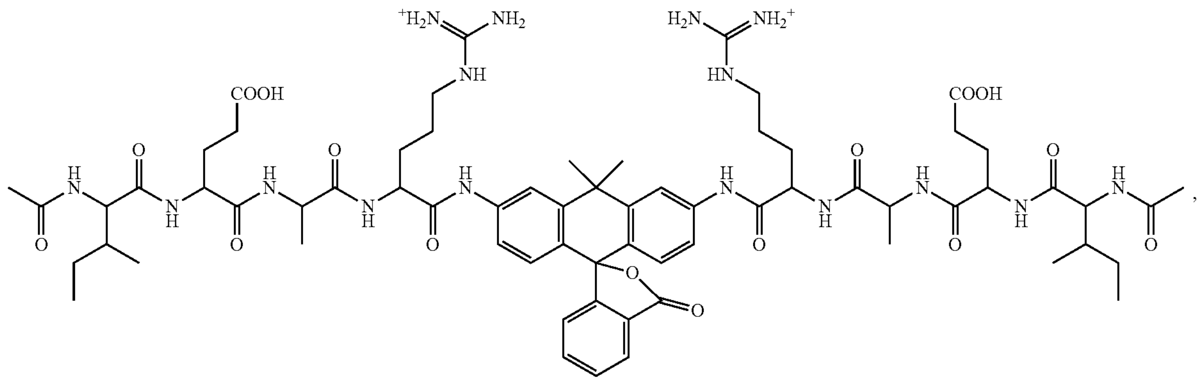
(20)
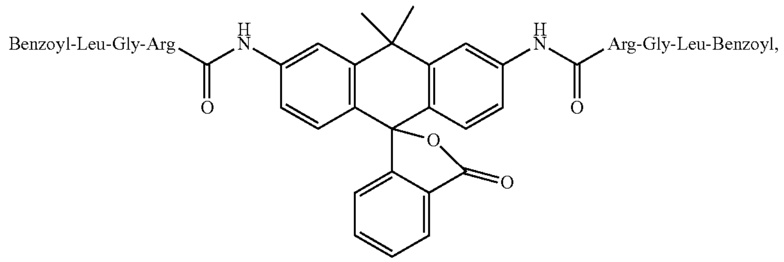
(21)
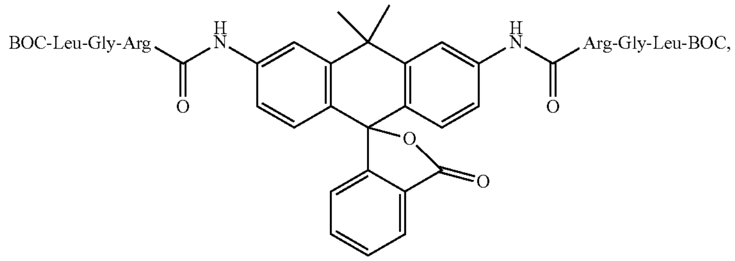
(26) (SEQ ID NO: 18)
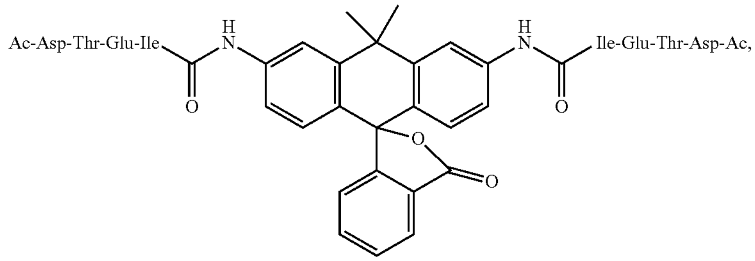
(30) (SEQ ID NO: 19)
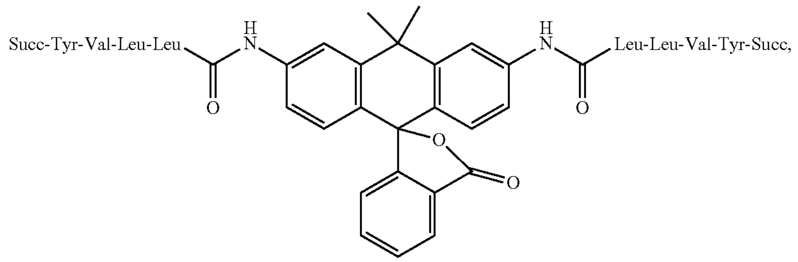

-continued (31)

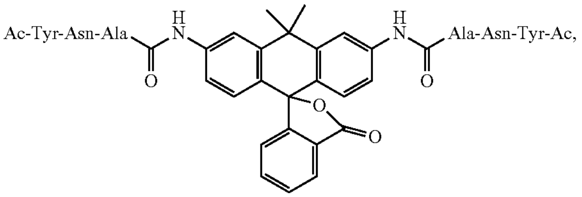

(34)

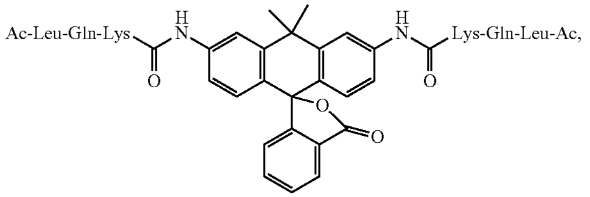

(35)

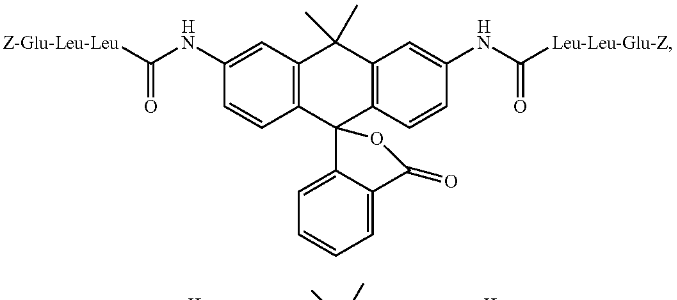

(36)

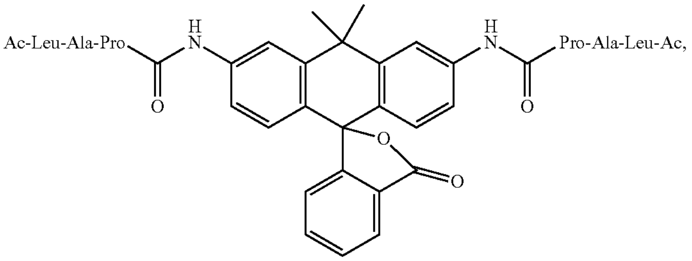

and (37)

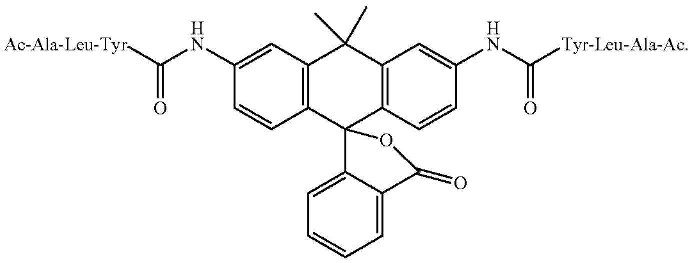

Clause 16. The compound clause 1, wherein the compound is of Formula (IB):

(IB)

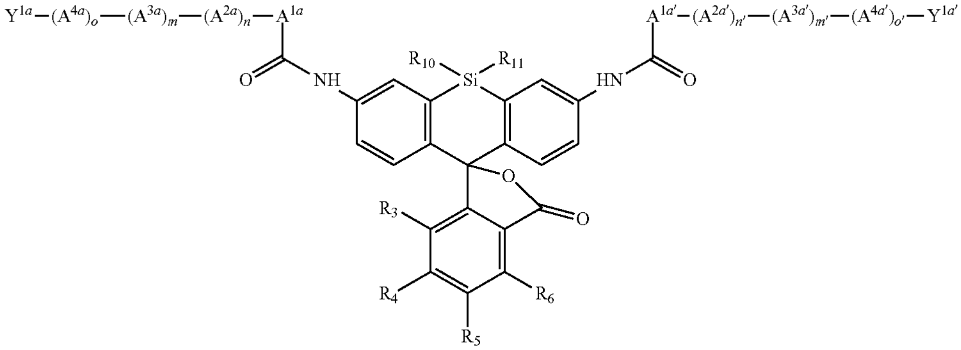

wherein:

$A^{1a}$-$A^{4a}$ and $A^{1a'}$-$A^{4a'}$ are each independently selected from an amino acid;

$Y^{1a}$ and $Y^{1a'}$ are each an optional terminal group;

$R_{10}$-$R_{11}$ are selected from H, alkyl and substituted alkyl; and n-o and n'-o' are each independently selected from 0 or 1.

Clause 17. The compound of clause 16, wherein $A^{1a}$-$A^{4a}$ and $A^{1a'}$-$A^{4a'}$ are each independently an amino acid selected from Alanine (Ala), isoleucine (Ile), leucine (Leu), valine (Val), tryptophan (Trp), asparagine (Asn), glutamine (Gln), proline (Pro), glycine (Gly), lysine (Lys), aspartic acid (Asp), glutamic acid (Glu) histidine (His), and arginine (Arg).

Clause 18. The compound of clause 17, wherein $A^{11}$-$A^{4a}$ and $A^{1a'}$-$A^{4a'}$ are each independently an amino acid selected from glycine (Gly), arginine (Arg), proline (Pro), valine (Val), lysine (Lys), leucine (Leu), histidine (His), and aspartic acid (Asp).

Clause 19. The compound of any one of clauses 15 to 17, wherein $A^{1a}$-$A^{4a}$ and $A^{1a'}$-$A^{4a'}$ are the same.

Clause 20. The compound of any one of clauses 16 to 19, wherein n-o and n'-o' are each 0.

Clause 21. The compound of clause 20, wherein $A^{1a}$ and $A^{1a'}$ are each selected from glycine (Gly), arginine (Arg), leucine, and (Leu, proline (Pro).

Clause 22. The compound of any one of clauses 16 to 21, wherein $Y^{1a}$ and $Y^{1a'}$ are each independently selected from alkyl, alkoxy, aryl, heteroaryl, amino, acyl, ester, wherein any of the $Y^{1a}$ and $Y^{1a'}$ groups are optionally further substituted.

Clause 23. The compound of any one of clauses 16 to 22, wherein $R^{10}$-$R^{11}$ are each alkyl.

Clause 24. The compound of clause 23, wherein each alkyl group is methyl.

Clause 25. The compound of any one of clauses 16 to 24, wherein $R_3$-$R_6$ are each H.

Clause 26. The compound of any one of clauses 16 to 25, wherein the compound is selected from one of the following structures:

(8)

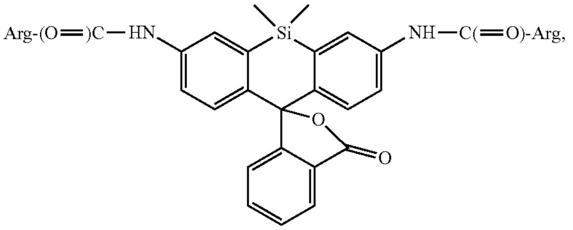

(9)

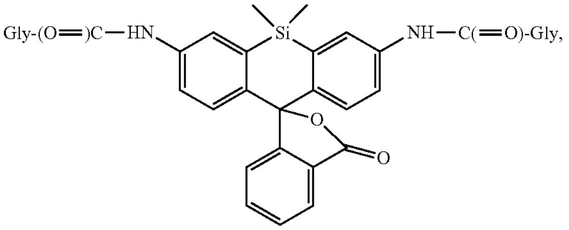

(22)

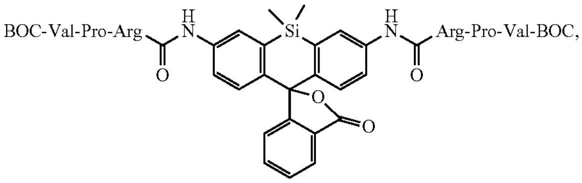

(23)

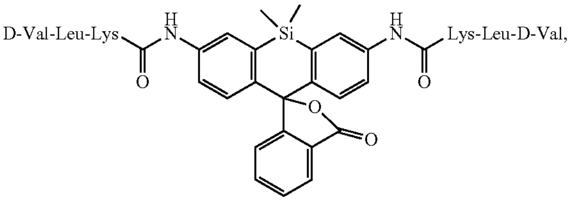

(27) (SEQ ID NO: 20)

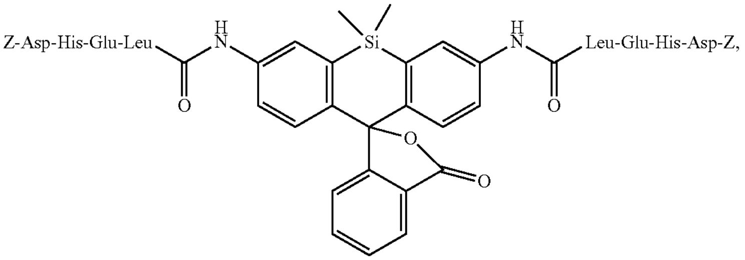

-continued (28)

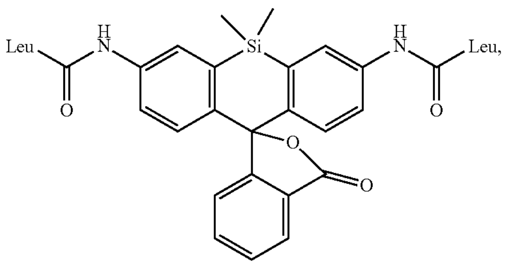

(32)

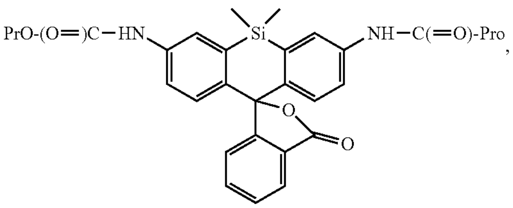

, and (39)

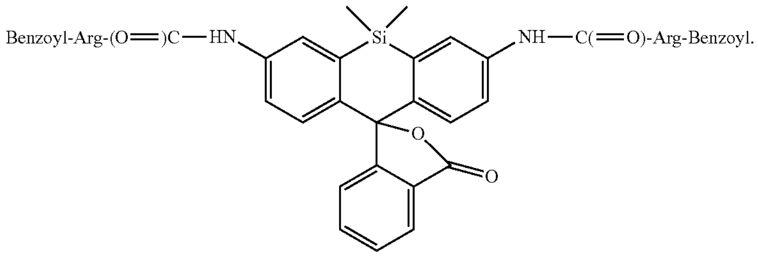

Clause 27. The compound of any one of clauses 1 to 26, wherein the compound is capable of detecting a protease activity, an apoptosis, or a cell viability in a bioassay.

Clause 28. The compound of clause 1, wherein the compound is of Formula 2:

(2)

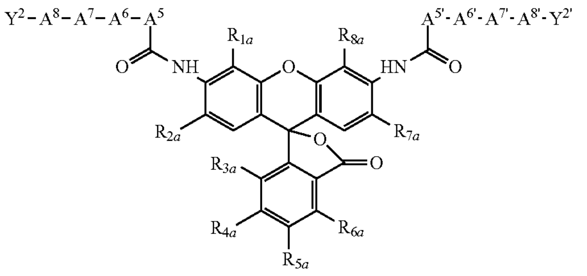

or a salt thereof, wherein:

$A^5$ and $A^{5'}$ are each arginine (Arg);

$A^6$-$A^8$ and $A^{6'}$-$A^{8'}$ are each independently selected from an amino acid;

$Y^2$ and $Y^{2'}$ is an optional terminal group; and $R^{1a}$-$R^{8a}$ are selected from hydrogen, halogen, a carboxy, an alkyl, a substituted alkyl, an aryl, a substituted aryl, a heteroaryl group and a substituted heteroaryl group.

Clause 29. The compound of clause 28, wherein $A^6$-$A^8$ are each independently selected from arginine (Arg), alanine (Ala), glutamic acid (Glu), and isoleucine (Ile).

Clause 30. The compound of clause 28 or 29, wherein $R^{1a}$-$R^{8a}$ are each H.

Clause 31. The compound of any one of clauses 28 to 30, wherein $Y^2$ and $Y^{2'}$ are each independently selected from alkyl, alkoxy, aryl, heteroaryl, amino, acyl, ester, wherein any of the $Y^2$-$Y^{2'}$ groups are optionally further substituted.

Clause 32. The compound of any one of clauses 28 to 31, wherein the compound is of Formula 2A:

Formula 2A

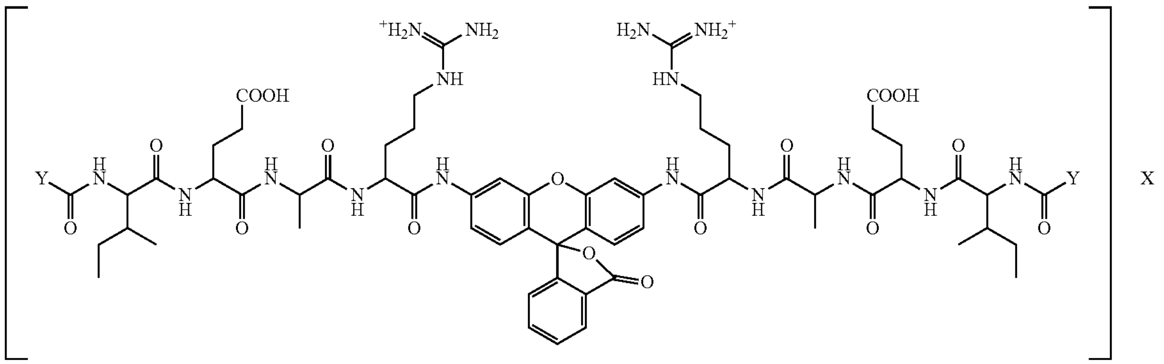

wherein:

X is a physiologically acceptable counter ion;

each Y is independently an alkyl, an aryl, a heteroaryl, an O-alkyl, an O-aryl, an O-heteroaryl, a NH-alkyl, a NH-aryl, or a NH-heteroaryl, wherein any of the Y groups are optionally substituted.

Clause 33. The compound of any one of clauses 28 to 32, wherein the compound is capable of detecting an endotoxin activity in an assay.

Clause 34. The compound of clause 32 or 33, wherein:

Y is a methyl, ethyl, $PhCH_2O$, or $(CH_3)_3CO$; and

X is chloride, nitrate, iodide, fluoride, phosphate, sulfate, acetate, trifluoroacetate, borate or tetrafluoroborate.

Clause 35. The compound of clause 32, wherein the compound is of the following structure:

a) contacting said sample with a detection reagent comprising a compound according to any one of clauses 28 to 36 under conditions in which said compound releases the detectable chromophore and/or fluorophore in the presence of endotoxin in the sample to produce an optical signal; and b) detecting the endotoxin level in the sample by detecting the optical signal.

Clause 43. The method of clause 42, wherein:

the detection reagent comprises limulus amebocyte lysate (LAL) that is activated in the presence of endotoxin; and the compound is of clause 32 or 35.

Clause 44. A kit for detecting a biological activity in a sample, the kit comprising:

(7)

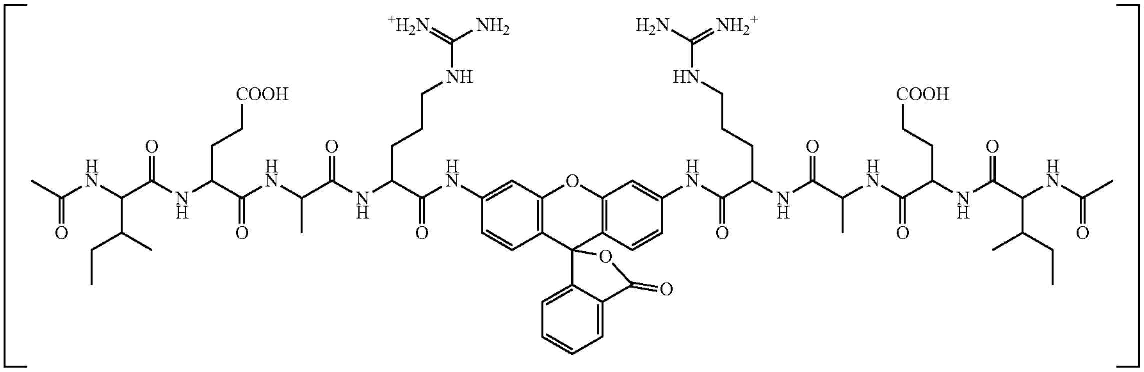

X.

Clause 36. The compound of any one of clauses 28 to 35, wherein the compound exists as an inner salt.

Clause 37. A method of detecting a biological activity in a sample, the method comprising:

a) contacting the sample with a detection reagent comprising a compound according to any one of clauses 1 to 36 under conditions in which said detection reagent releases the detectable chromophore and/or fluorophore in the presence of a target analyte, if present in the sample, to produce an optical signal; and b) assessing whether the target analyte is present in the sample by detecting the optical signal.

Clause 38. The method of clause 37, wherein the target analyte is a protease.

Clause 39. The method of clause 37, further comprising assessing a biological activity in the sample.

Clause 40. The method of clause 39, wherein the biological activity is an apoptosis.

Clause 41. The method of clause 39, wherein the biological activity is a cell viability.

Clause 42. A method of determining an endotoxin level in a sample, comprising a) one or more compounds according to any one of clauses 1 to 36; and b) one or more components selected from a buffer, an organic solvent, one or more detection reagents, luminescence standards, an enzyme, an enzyme indicator and an instruction sheet concerning the use of the kit for detecting a biological activity in a sample.

Clause 45. The kit of clause 44, comprising:

a) a compound of clause 32 or 35; and b) limulus amebocyte lysate (LAL) and an instruction sheet concerning the use of the kit for detecting endotoxin in a sample.

EXAMPLES

Examples of some synthetic strategies for selected substrates of the invention, as well as their characterization, synthetic precursors and methods of use are provided in the examples below. Further modifications and permutations will be obvious to one skilled in the art. The examples below are given so as to illustrate the practice of this invention. They are not intended to limit or define the entire scope of this invention. It is to be understood that this invention is not limited to particular aspects described, as such may vary. It is also to be understood that the terminology used herein is for the purpose of describing particular aspects only and is not intended to be limiting since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Synthesis of the substrates of the invention depends on initial preparation of certain key intermediates. For simplicity, all but a few of the possible substituents are shown as hydrogen. These basic structures are optionally further substituted, during or after synthesis, to give the corresponding polymer conjugate substituents as defined above. It is recognized that there are many possible variations that may yield equivalent results.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two- or three-dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

Example 1. The Preparation of Compound 2

2

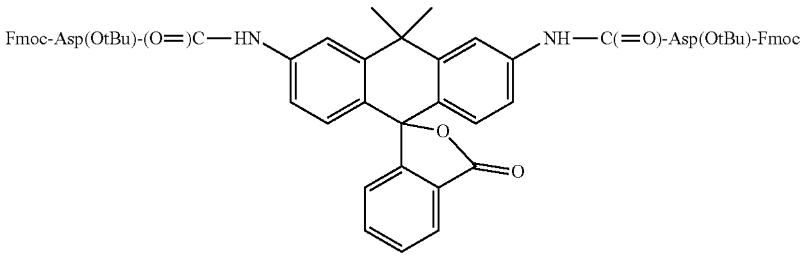

2-(6-amino-3-iminio-10,10-dimethyl-3,10-dihydroanthracen-9-yl)benzoate is prepared as described by Jonathan B. et al., ACS Chemical Biology 2013, 8, 1303-1310. The dihydroanthracen-9-yl compound is mixed with HOBt (52 mg), Fmoc-Asp(OtBu)-OH (157 mg) in 2 mL DMF and 2 mL pyridine. The mixture is cooled in an ice bath and EDC (81 mg) is added. The reaction is stirred at room temperature for 1 hour before being diluted by EtOAc, washed by water, 1N HCl, saturated $NaHCO_3$ solution and brine. The organic phase is separated, collected and dried over anhydrous sodium sulfate. The dried EtOAc solution is filtered and concentrated to give the crude product. The crude product is purified on a silica gel column (hexane-EtOAc, 0% to 50%) to give compound 2 as a white solid.

Example 2. The Preparation of Compound 3

3

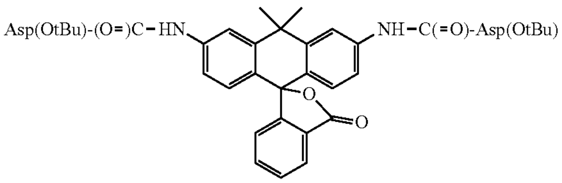

Piperidine (0.017 mL) is added to compound 2 (88 mg) in 3 mL DMF. The mixture is stirred at room temperature for 5 minutes before being concentrated. The crude product is purified on a silica gel column (DCM-MeOH, 0% to 10%) to give compound 3 as a colorless oil.

Example 3. The Preparation of Compound 4 (SEQ ID NO: 16)

4

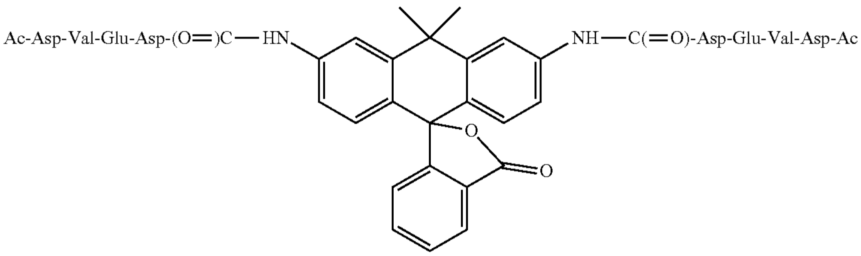

Compound 3 (58 mg) is mixed with HOBt (34 mg), Fmoc-Asp(OtBu)-Glu(OtBu)-Val-OH (173 mg, Biomer Technology) in 2 mL DMF and 2 mL pyridine. The mixture is cooled in an ice bath, and EDC (48 mg) is added. The reaction mixture is stirred at room temperature for 1 hour before being diluted with EtOAc, and washed with water, 1N HCl, saturated $NaHCO_3$ and brine. The organic phase is separated, and dried over anhydrous sodium sulfate, filtered and concentrated to give a crude solid. The crude solid is dissolved in DMF (4 mL). To the DMF solution, piperidine (0.25 mL) is added. The mixture is stirred at room temperature for 5 minutes and then concentrated to give an oil. To this oil are added 4 mL pyridine and 2 mL $Ac_2O$. The mixture is stirred at room temperature for 10 minutes and then concentrated. The residue is added to 6 mL dichloromethane, 1 mL anisole and 6 mL trifluoroacetic acid. The solution is stirred at room temperature for 7 hours and then concentrated to give the crude product, which is further purified by HPLC (C18 column, and TEAB buffer-MeCN, 0% to 20%) and lyophilized to give the desired Compound 4 (SEQ ID NO: 16) as an off-white solid.

Example 4. The Preparation of Compound 5

8

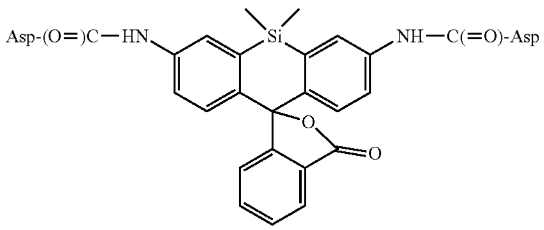

Compound 2 (20 mg) is dissolved in 6 mL dichloromethane at room temperature. To the dichloromethane solution are added 1 mL anisole and 6 mL trifluoroacetic acid. The solution is stirred at room temperature until the reaction is complete. The reaction mixture is concentrated to give the crude product, which is further purified by HPLC (C18 column, and TEAB buffer-MeCN, 0% to 20%) and lyophilized to give the desired Compound 5 as an off-white solid.

Example 5. The Preparation of Compound 6 (SEQ ID NO: 17)

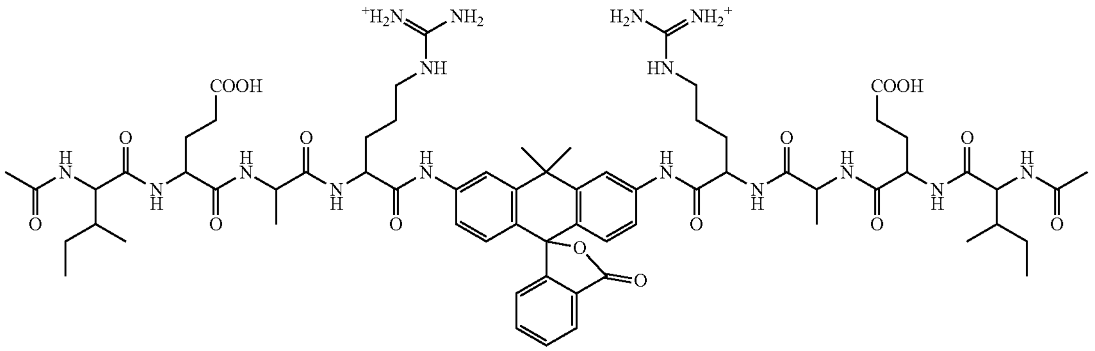 [SMILES: CCC(C)C(NC(C)=O)C(=O)NC(CCC(=O)O)C(=O)NC(C)C(=O)NC(CCCNC(N)=[NH2+])C(=O)Nc1ccc2c(c1)C(C)(C)c1cc(NC(=O)C(CCCNC(N)=[NH2+])NC(=O)C(C)NC(=O)C(CCC(=O)O)NC(=O)C(NC(C)=O)C(C)CC)ccc1C21OC(=O)c2ccccc21]

2-(6-amino-3-iminio-10,10-dimethyl-3,10-dihydroanthracen-9-yl)benzoate (50 mg) is dissolved in DMF (5 mL). To the DMF solution, are added EDC (300 mg), Ac-Ile-Glu(OtBu)-Ala-Arg-OH (500 mg, Biomer Technology) and 2 mL pyridine. The reaction is stirred at room temperature for 1 hour before being diluted by EtOAc, washed by water, 1N HCl, saturated $NaHCO_3$ solution and brine. The organic phase is separated, collected and dried over anhydrous sodium sulfate. The dried EtOAc solution is filtered and concentrated to give the crude solid. The crude solid is purified on a silica gel column (hexane-EtOAc, 0% to 50%) to give an off-white solid. The solid is added to 6 mL dichloromethane, 1 mL anisole and 6 mL trifluoroacetic acid. The solution is stirred at room temperature for 7 hours and then concentrated to give the crude product, which is further purified by HPLC (C18 column, and TEAB buffer-MeCN, 0% to 20%) and lyophilized to give the desired Compound 6 (SEQ ID NO: 17) as an off-white solid.

Example 6. The Preparation of Compound 7 (SEQ ID NO: 21)

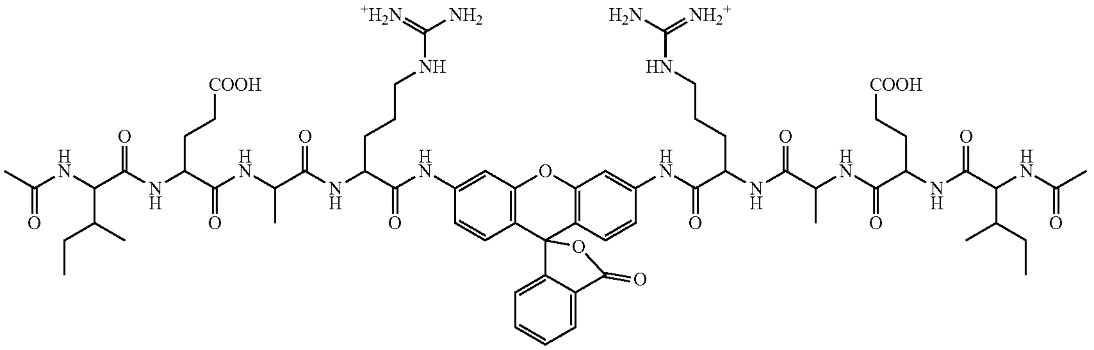 [SMILES: CCC(C)C(NC(C)=O)C(=O)NC(CCC(=O)O)C(=O)NC(C)C(=O)NC(CCCNC(N)=[NH2+])C(=O)Nc1ccc2c(c1)Oc1cc(NC(=O)C(CCCNC(N)=[NH2+])NC(=O)C(C)NC(=O)C(CCC(=O)O)NC(=O)C(NC(C)=O)C(C)CC)ccc1C21OC(=O)c2ccccc21]

Rhodamine 110 (50 mg) is mixed with HOBt (250 mg), Ac-Ile-Glu(OtBu)-Ala-Arg-OH (500 mg) in 2 mL DMF and 2 mL pyridine. The mixture is cooled in ice bath and EDC (300 mg) is added. The reaction is stirred at room temperature for 1 hour before being diluted by EtOAc, washed by water, 1N HCl, saturated $NaHCO_3$ solution and brine. The organic phase is separated, collected and dried over anhydrous sodium sulfate. The dried EtOAc solution is filtered and concentrated to give the crude solid. The crude solid is purified on a silica gel column (hexane-EtOAc, 0% to 50%) to give an off-white solid. The solid is added to 6 mL dichloromethane containing 1 mL anisole and 6 mL trifluoroacetic acid. The solution is stirred at room temperature for 7 hours and then concentrated to give the crude product, which is further purified by HPLC (C18 column, and TEAB buffer-MeCN, 0% to 20%) and lyophilized to give the desired Compound 7 (SEQ ID NO: 21) as an off-white solid.

Example 7. The Preparation of Compound 8

8

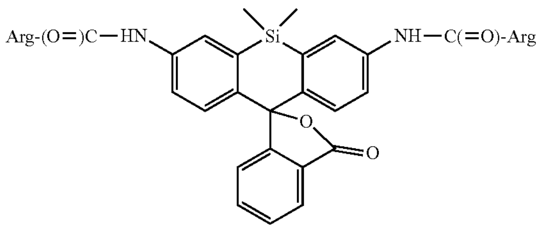

2-(7-amino-3-iminio-5,5-dimethyl-3,5-dihydrodibenzo[b,e]silin-10-yl)benzoate is prepared as described by Lavis L. et al., U. S. Pat. Appl. No. 20210085805. The dihydrodibenzo[b,e]silin-10-yl compound is mixed with HOBt (50 mg), Fmoc-Arg-OH (300 mg) in 2 mL DMF and 2 mL pyridine. The mixture is cooled in ice bath and EDC (81 mg) is added. The reaction is stirred at room temperature for 1 hour before being diluted by EtOAc, washed by water, 1N HCl, saturated $NaHCO_3$ solution and brine. The organic phase is separated, collected and dried over anhydrous sodium sulfate. The dried EtOAc solution is filtered and concentrated to give the crude product. The crude product is purified on a silica gel column (hexane-EtOAc, 0% to 50%) to give a white solid. The white solid is dissolved in 5 mL DMF. To the DMF solution, piperidine (0.5 mL) is added. The mixture is stirred at room temperature until the FMOC deprotection is completed. The crude solid is further purified by HPLC (C18 column, and TEAB buffer-MeCN, 0% to 20%) and lyophilized to give the desired Compound 8 as an off-white solid.

Example 8. The Preparation of Compound 9

9

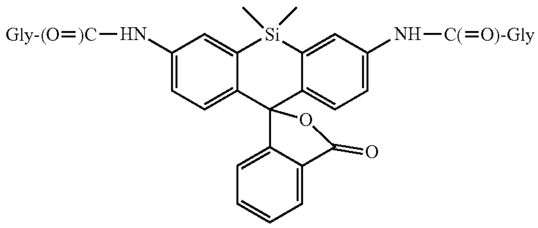

2-(7-amino-3-iminio-5,5-dimethyl-3,5-dihydrodibenzo[b,e]silin-10-yl)benzoate is mixed with HOBt (50 mg), Boc-Gly-OH (300 mg) in 2 mL DMF and 2 mL pyridine. The mixture is cooled in ice bath and EDC (81 mg) is added. The reaction is stirred at room temperature for 1 hour before being diluted by EtOAc, washed by water, 1N HCl, saturated $NaHCO_3$ solution and brine. The organic phase is separated, collected and dried over anhydrous sodium sulfate. The dried EtOAc solution is filtered and concentrated to give the crude product. The crude product is purified on a silica gel column (hexane-EtOAc, 0% to 50%) to give a white solid.

The solid is added to 5 mL dichloromethane containing 1 mL anisole and 6 mL trifluoroacetic acid. The solution is stirred at room temperature until the BOC deprotection is completed. The crude solid is further purified by HPLC (C18 column, and TEAB buffer-MeCN, 0% to 20%) and lyophilized to give the desired Compound 9 as an off-white solid.

Example 9. Staining of Live Cells with Compound 9

Figure 4:
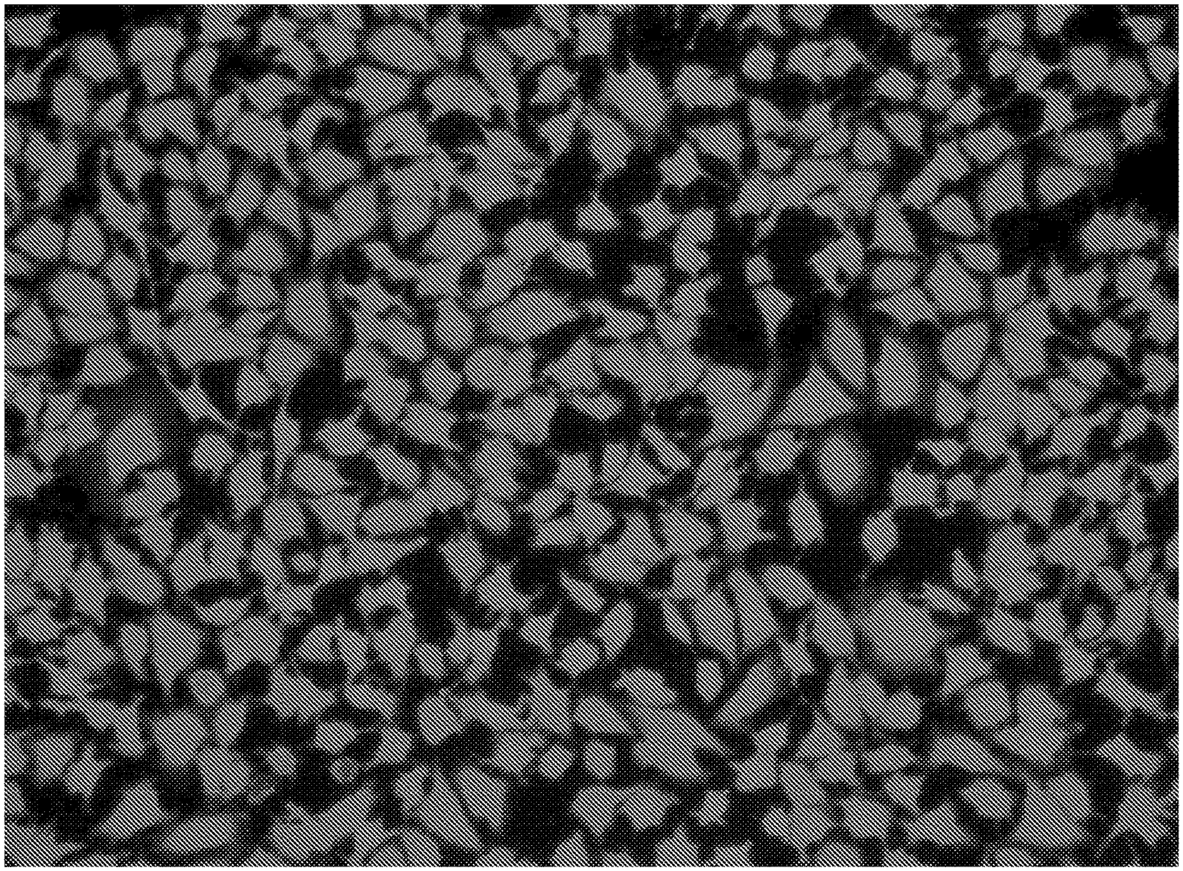
FIG. 4. Illustrates the detection of aminopeptidase activity with an exemplary compound. HL-60 cells (about $2\times10^6$) are incubated with 10 μM of Compound 9 for 2 hours at 37° C. in a $CO_2$ incubator. At the end of the incubation, the cells are harvested by centrifugation and resuspended in 50 μL of fresh medium without substrate. Aliquots of each cell suspension are placed in microslides and viewed on a Keyence inverted microscope with epifluorescent illumination. Cells incubated with Compound 9 exhibits a strong, homogeneously distributed, red fluorescence, indicating that Compound 9 can be used to detect aminopeptidase activity in whole cells.
Figure 5:
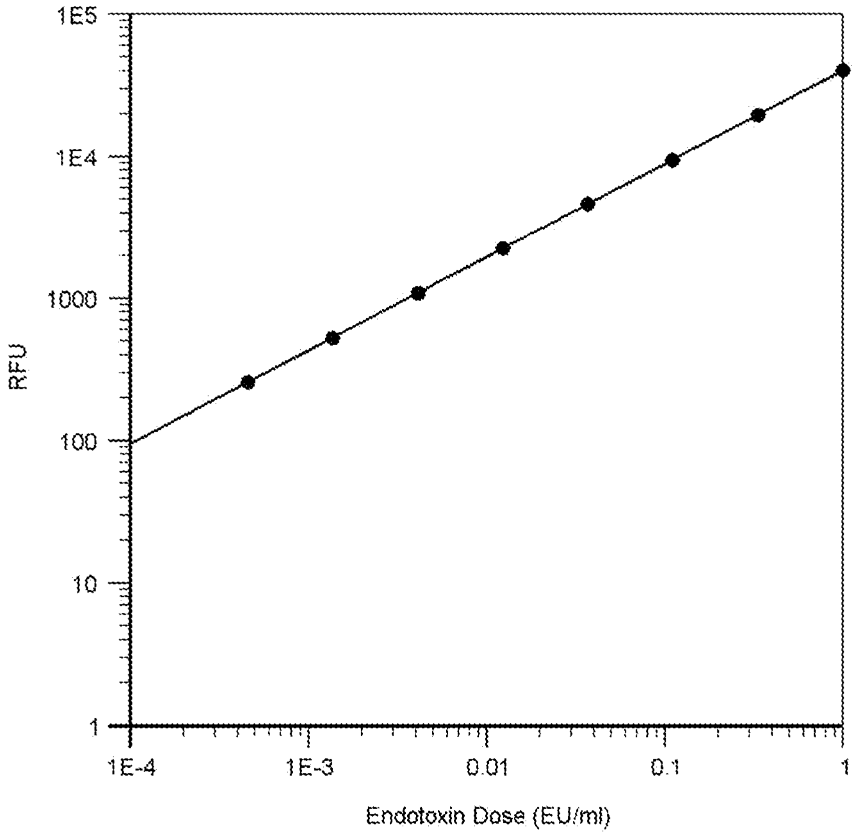
FIG. 5. Illustrates the detection of *E. coli* endotoxin with an exemplary compound. *E. coli* endotoxin is measured in a black/solid bottom 96-well plate with Compound 7. The fluorescence intensity is recorded using a Gemini microplate reader at Ex/Em=490/525 nm, cutoff=515 nm. As low as 0.001 EU/mL of *E. coli* endotoxin can be detected.

HL-60 cells (about $2\times10^6$) are incubated with 10 μM of Compound 9 for 2 hours at 37° C. in a $CO_2$ incubator. At the end of the incubation, the cells are harvested by centrifugation and resuspended in 50 μL of fresh medium without substrate. Aliquots of each cell suspension are placed in microslides and viewed on a Keyence inverted microscope with epifluorescent illumination. Cells incubated with Compound 9 exhibits a strong, homogeneously distributed, red fluorescence, indicating that Compound 9 can be used to detect aminopeptidase activity in whole cells. FIG. 4 shows that fluorescence imaging of cells Compound 9 under whole cell assay conditions.

Example 10. Detection of Apoptosis with Compound 4 in a Whole Cell Assay

Jurkat T leukemia cells are grown in RPMI 1640 media (Life Technologies, Inc.) and 10% FCS (Sigma Chemical Company) in a 5% $CO_2$-95% humidity incubator at 37° C., and maintained at a cell density between 4 and $8\times10^5$ cells/ml. Cells were harvested at 200×g and resuspended at $1\times10^6$ cells/ml into RPMI 1640 media containing 10% FCS and 1 ml each were dispensed in 2-wells of a 6-well plate. The apoptosis inducer staurosporine is added at 0.5 μg/ml concentration and the plate is incubated for 2 hours at 37° C. in a 5% $CO_2$-95% humidity incubator. Cells are incubated with 50 μM of substrate Compound 4 for 2 hours at 37° C. in serum-free RPMI medium. The samples are analyzed with a fluorescence microplate reader (top or bottom read mode) at Ex/Em=540/620 nm (Cutoff=610 nm). FIG. 4 shows that induction of apoptosis in Jurkat cells by staurosporine leads to cleavage of the caspase-3/7 substrate Compound 4 under whole cell assay conditions.

Example 11. Detection of Endotoxin with Compound 7

Endotoxin is the major component of the outer membrane of Gram-negative bacteria. endotoxin is a potent stimulator of the vertebrate innate immune system and can cause fever, septic shock and eventually death. It is recognized as a biomarker for the detection of bacterial pathogen invasion and is responsible for the development of inflammatory response and endotoxic shock in extreme cases. Detection of endotoxin in biological materials, such as protein, peptide or antibody sample, is a critical task in biological manufacturing and processing. Compound 7 is hydrolyzed in the presence of endotoxins by the Limulus Amebocyte Lysate (LAL), an extract of blood cells from a horseshoe crab. The LAL enzymatic cascade can be activated by endotoxin at pH 6.0 to 7.5, and the amount of activated enzyme present can be measured by its ability to cleave the fluorogenic and/or chromogenic substrate. Rhodamine 110 is identified as the hydrolyzed product of Compound 7, generating strong green fluorescence. The endotoxin activity is proportional to the fluorescence intensity of rhodamine 110 resulting from the hydrolysis of Compound 7. The concentration of endotoxin in a sample can be calculated from a standard curve. A test sample is properly treated to a solution that is mixed with LAL (100 U). The resulted solution is incubated at 37° C. for 30 to 60 minutes and mixed with 10 uM working solution of Compound 7 that is prepared from 5 mM DMSO stock solution of Compound 7 with endotoxin-free water. The fluorescence intensities of the test sample solutions are recorded with a fluorescence microplate reader at Ex/Em=490/525 nm within 10-30 minutes.

In is noted that under the same conditions compounds (i)-(xiii) according to the following formula did not demonstrate a useful signal for detecting endotoxin activity:

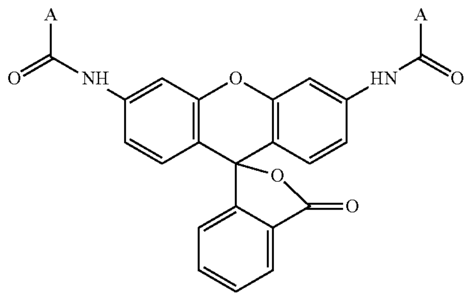

wherein A in each of compounds (i)-(xiii) is the same and selected from:

```
(i)
Beta-Ala-*,

(ii)
Ala-*,

(iii)
                                        (SEQ ID NO: 22)
Ac-Leu-Glu-His-Asp-*,

(iv)
                                        (SEQ ID NO: 23)
Cbz-Asp-Glu-Val-Asp-*,

(v)
                                        (SEQ ID NO: 24)
Ac-Ile-Glu-Thr-Asp-*,

(vi)
Ac-Ala-Asn-Trp-*,

(vii)
BOC-Val-Pro-Arg-*,

(viii)
Ac-Lys-Gln-Leu-*,

(ix)
Cbz-Leu-Leu-Glu-*,

(x)
Ac-Pro-Ala-Leu-*,

(xi)
Ac-Trp-Leu-Ala-*,

(xii)
Ac-Lys-His-Leu-*,
and

(xiii)
                                        (SEQ ID NO: 25)
Succ-Lys-His-Leu-Tyr-*,
```

where * represents the point of attachment to the carboxamide carbons on the rhodamine core.

What is claimed is:

1. A chromogenic and/or fluorogenic compound having the structure of Formula 1:

Formula 1

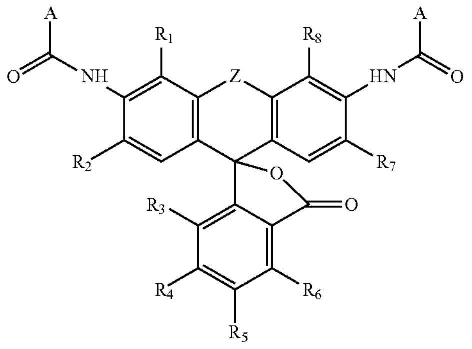

or a salt thereof, wherein:

each A is an amino acid or a peptide fragment connected to a masked chromophore and/or fluorophore moiety via an enzyme-cleavable amide bond;

$R_1$ to $R_8$ are each independently selected from hydrogen, halogen, a carboxy, an alkyl, a substituted alkyl, an aryl, a substituted aryl, a heteroaryl group, and a substituted heteroaryl group; and Z is $C(R_{10}R_{11})$, wherein $R_{10}$ and $R_{11}$ are independently selected from hydrogen, an alkyl, a substituted alkyl, an aryl, a substituted aryl, a heteroaryl group and a substituted heteroaryl group; and wherein the compound is capable of releasing a detectable chromophore and/or fluorophore in the presence of a target enzyme or analyte that provides for cleavage of the enzyme-cleavable amide bonds.

2. The compound of claim 1, wherein:

$R_1$ to $R_8$ are independently selected from H, F, Cl, a methyl, and a carboxy; and $R_{10}$ and $R_{11}$ are each alkyl.

3. The compound of claim 1, wherein:

each A is a peptide fragment comprising one or more amino acids selected from Arg, Ala, Pro, D-Ala, Beta-Ala and Asp;

$R_1$ to $R_8$ are each H; and $R_{10}$ and $R_{11}$ are each methyl.

4. The compound of claim 1, wherein:

each A is selected from Ac-Ala-Asn-Trp, Cbz-Asp-Glu-Val-Asp, Ac-Asp-Glu-Val-Asp, succinimidyl-Leu-Leu-Val-Tyr, Ac-Trp-Leu-Ala, Ac-Lys-Gln-Leu, Cbz-Leu-Leu-Glu, Ac-Pro-Ala-Leu, Ac-Ile-Thr-Asp, Ac-Arg-Arg-Arg, Boc-Leu-Leu-Val-Tyr, Ac-Leu-Glu-His-Asp, Gly-Pro, Cbz-Leu-Arg-Gly-Gly, Cbz-Lys-Lys-Ala-Gly, and Cbz-Lys-Ala-Gly-Gly;

$R_1$ to $R_8$ are each H; and $R_{10}$ and $R_{11}$ are each methyl.

5. The compound of claim 1, wherein the compound is of the formula (IA):

(IA)

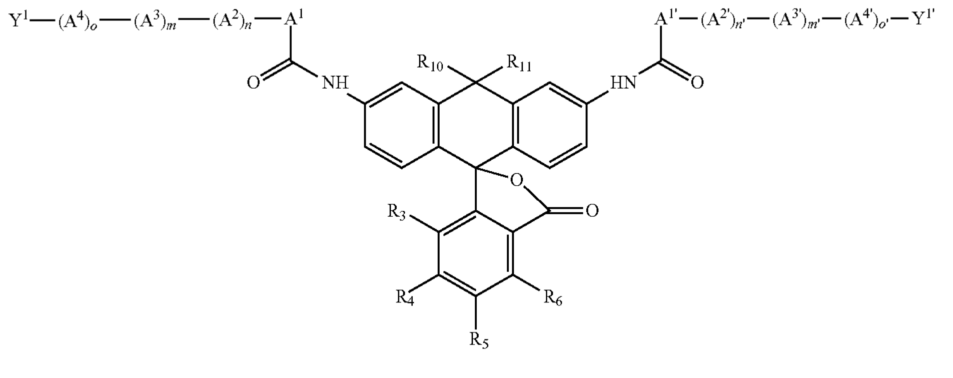

wherein:

$A^1$-$A^4$ and $A^{1'}$-$A^{4'}$ are each independently selected from an amino acid;

$Y^1$ and $Y^{1'}$ are each an optional terminal group;

$R^{10}$ and $R^{11}$ are independently selected from H, alkyl and substituted alkyl; and n-o and n'-o' are each independently selected from 0 or 1.

6. The compound of claim 5, wherein $A^1$-$A^4$ and $A^{1'}$-$A^{4'}$ are each independently an amino acid selected from Alanine (Ala), isoleucine (Ile), leucine (Leu), valine (Val), tryptophan (Trp), asparagine (Asn), glutamine (Gln), proline (Pro), glycine (Gly), lysine (Lys), aspartic acid (Asp), glutamic acid (Glu) and arginine (Arg), wherein the amino acid is of L-configuration or D-configuration.

7. The compound of claim 5, wherein $A^1$-$A^4$ and $A^{1'}$-$A^{4'}$ are each selected from Asp-Glu-Val-Asp and Arg-Ala-Glu-Ile.

8. The compound of claim 1, wherein $R^{10}$ and $R^{11}$ are independently selected from H, alkyl and substituted alkyl.

9. The compound of claim 1, wherein the compound is selected from:

| Cpd # | Structure |
|---|---|
| 4 | 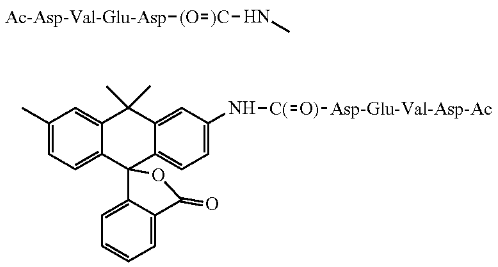 |
| 5 | 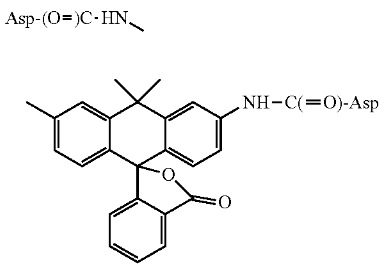 |

-continued

| Cpd # | Structure |
|---|---|
| 6 | 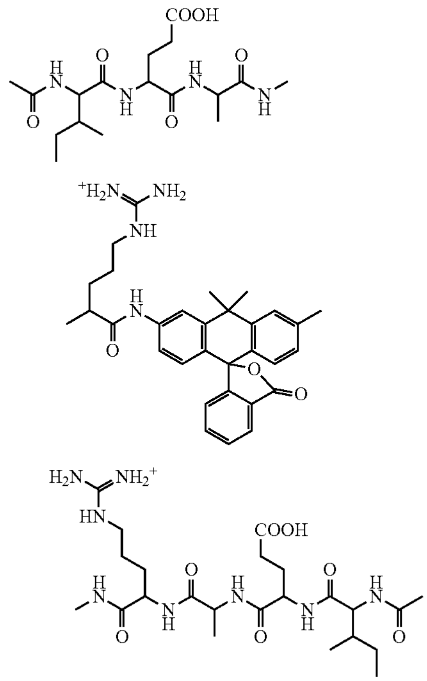 |
| 20 | 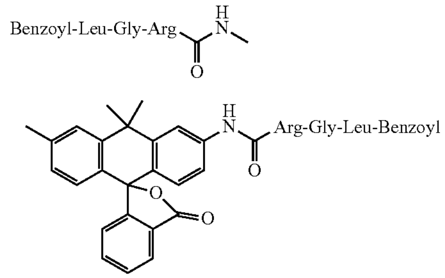 |

-continued

| Cpd # | Structure |
|---|---|
| 21 | 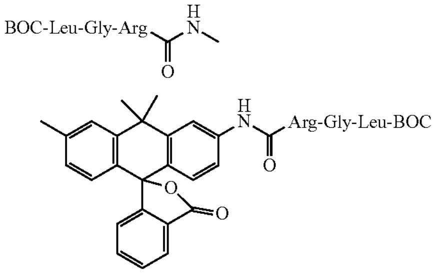 |
| 26 | 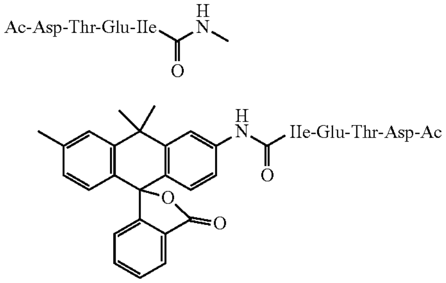 |
| 30 | 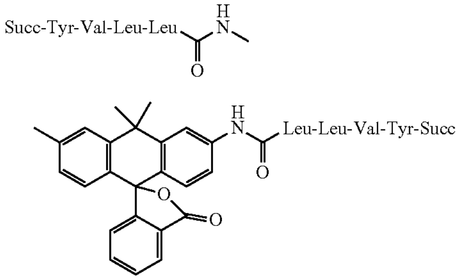 |
| 31 | 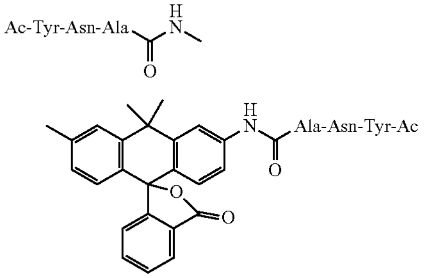 |
| 34 | 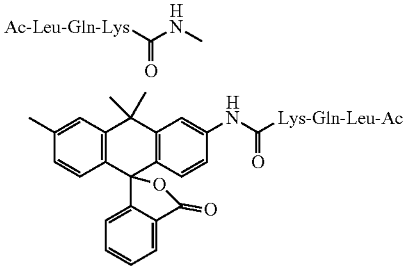 |

-continued

| Cpd # | Structure |
|---|---|
| 35 | 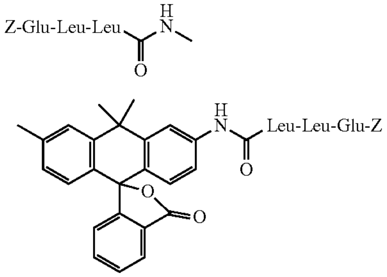 |
| 36 | 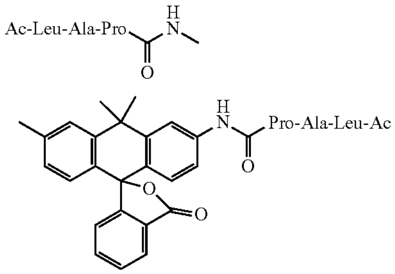<br>and |
| 37 | 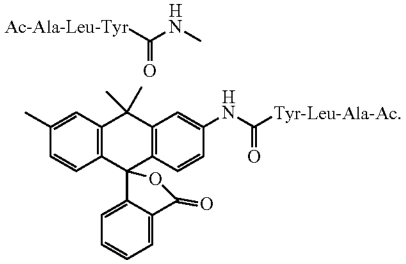 |

10. A method of detecting a biological activity in a sample, the method comprising:

a) contacting the sample with a detection reagent comprising a compound according to claim 1 under conditions in which said detection reagent releases the detectable chromophore and/or fluorophore in the presence of a target analyte, if present in the sample, to produce an optical signal; and b) assessing whether the target analyte is present in the sample by detecting the optical signal.

11. The method of claim 10, wherein the target analyte is a protease.

12. The method of claim 10, further comprising assessing a biological activity in the sample.

13. The method of claim 12, wherein the biological activity is an apoptosis or cell viability.

14. A method of determining an endotoxin level in a sample, comprising:

a) contacting said sample with a detection reagent comprising a compound according to claim 1 under conditions in which said compound releases the detectable chromophore and/or fluorophore in the presence of endotoxin in the sample to produce an optical signal; and b) detecting the endotoxin level in the sample by detecting the optical signal.

15. A kit for detecting a biological activity in a sample, the kit comprising:

a) one or more compounds according to claim 1; and b) one or more components selected from a buffer, an organic solvent, one or more detection reagents, luminescence standards, an enzyme, an enzyme indicator and an instruction sheet concerning the use of the kit for detecting a biological activity in a sample.

* * * * *